United States Patent
Trees et al.

(10) Patent No.: US 9,675,405 B2
(45) Date of Patent: Jun. 13, 2017

(54) METHODS AND DEVICES FOR CONTROLLING MOTORIZED SURGICAL DEVICES

(71) Applicant: Ethicon Endo-Surgery, Inc., Cincinnati, OH (US)

(72) Inventors: Gregory A. Trees, Loveland, OH (US); Chad P. Boudreaux, Cincinnati, OH (US); Matthew C. Miller, Cincinnati, OH (US); Mark A. Davison, Mason, OH (US); David C. Yates, West Chester, OH (US); John A. Hibner, Mason, OH (US); Jill A. Inkrott-Smith, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 108 days.

(21) Appl. No.: 14/247,916

(22) Filed: Apr. 8, 2014

(65) Prior Publication Data

US 2015/0282823 A1    Oct. 8, 2015

(51) Int. Cl.
*A61B 17/285* (2006.01)
*A61B 18/14* (2006.01)
(Continued)

(52) U.S. Cl.
CPC  *A61B 18/1445* (2013.01); *A61B 2017/00026* (2013.01); *A61B 2018/0063* (2013.01);
(Continued)

(58) Field of Classification Search
CPC .......... A61B 17/285; A61B 2018/1226; A61B 18/1445; A61B 2017/2841;
(Continued)

(56) References Cited

U.S. PATENT DOCUMENTS

| 6,273,862 B1 | 8/2001 | Privitera et al. |
| 6,663,627 B2 | 12/2003 | Francischelli et al. |

(Continued)

FOREIGN PATENT DOCUMENTS

| WO | WO-2012012674 A1 | 1/2012 |

OTHER PUBLICATIONS

U.S. Appl. No. 14/166,194, filed Jan. 28, 2014.
(Continued)

*Primary Examiner* — Eric Rosen
*Assistant Examiner* — George J Ulsh
(74) *Attorney, Agent, or Firm* — Mintz Levin Cohn Ferris Glovsky and Popeo, P.C.

(57) ABSTRACT

Methods and devices for controlling motorized surgical devices are provided. In general, the methods and devices can allow a surgical device to grasp and cut tissue. In some embodiments, the device can include at least one sensor and a motor, and an output of the motor can be configured to be adjusted based at least in part on an output from the at least one sensor. The output of the motor can be configured to provide power for translation of a cutting element along an end effector of the device. Adjusting the motor's output can cause the cutting element to translate through the end effector at different speeds, thereby allowing the cutting element to cut through tissue being grasped by the end effector at different speeds.

23 Claims, 15 Drawing Sheets

(51) Int. Cl.
  *A61B 17/00* (2006.01)
  *A61B 18/00* (2006.01)
(52) U.S. Cl.
  CPC .............. *A61B 2018/00345* (2013.01); *A61B 2018/00494* (2013.01); *A61B 2018/00607* (2013.01); *A61B 2018/00875* (2013.01); *A61B 2018/1455* (2013.01)
(58) Field of Classification Search
  CPC  A61B 2018/00601; A61B 2017/00026; A61B 2018/00345; A61B 2018/00607; A61B 2018/0063; A61B 2018/00875; A61B 2018/1455
  USPC ......................................................... 606/170
  See application file for complete search history.

(56) References Cited

U.S. PATENT DOCUMENTS

| | | | |
|---|---|---|---|
| 7,416,101 | B2 | 8/2008 | Shelton, IV et al. |
| 7,776,037 | B2 | 8/2010 | Odom |
| 8,125,184 | B2 | 2/2012 | Raji et al. |
| 8,128,625 | B2 | 3/2012 | Odom |
| 8,357,158 | B2 | 1/2013 | McKenna et al. |
| 8,357,160 | B2 | 1/2013 | Odom |
| 2002/0107517 | A1 | 8/2002 | Witt et al. |
| 2003/0018331 | A1 | 1/2003 | Dycus et al. |
| 2004/0122423 | A1 | 6/2004 | Dycus et al. |
| 2008/0039836 | A1 | 2/2008 | Odom et al. |
| 2009/0182327 | A1 | 7/2009 | Unger |
| 2010/0217264 | A1 | 8/2010 | Odom et al. |
| 2011/0238056 | A1 | 9/2011 | Koss et al. |
| 2011/0295295 | A1 | 12/2011 | Shelton, IV et al. |
| 2012/0022524 | A1 | 1/2012 | Timm et al. |
| 2012/0022525 | A1 | 1/2012 | Dietz et al. |
| 2012/0078139 | A1 | 3/2012 | Aldridge et al. |
| 2012/0083784 | A1 | 4/2012 | Davison et al. |
| 2012/0116379 | A1 | 5/2012 | Yates et al. |
| 2012/0116380 | A1 | 5/2012 | Madan et al. |
| 2012/0143182 | A1 | 6/2012 | Ullrich et al. |
| 2012/0179151 | A1 | 7/2012 | Mueller |
| 2012/0310229 | A1 | 12/2012 | Gregg |
| 2013/0123783 | A1 | 5/2013 | Marczyk et al. |
| 2014/0005667 | A1 | 1/2014 | Stulen et al. |
| 2015/0282822 | A1 | 10/2015 | Trees et al. |
| 2015/0282824 | A1 | 10/2015 | Trees et al. |
| 2015/0282825 | A1 | 10/2015 | Trees et al. |

OTHER PUBLICATIONS

U.S. Appl. No. 14/166,244, filed Jan. 28, 2014.
International Search Report and Written Opinion for PCT/US2015/024450 mailed Sep. 28, 2015.

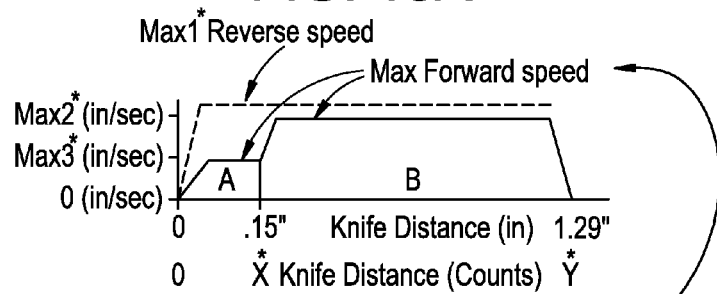
FIG. 13A
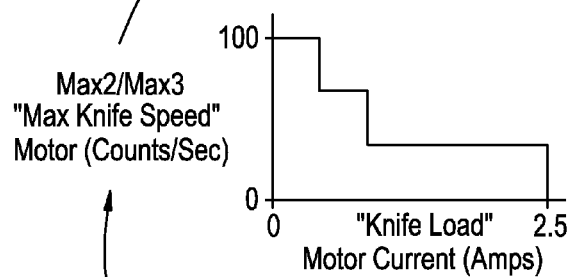
FIG. 13B
FIG. 13C
| Input | | Output | |
|---|---|---|---|
| Knife Load (lbf) —α— | Proportional to Motor Current (Amps)* | Max Knife Speed (in/sec) —α— | Proportional to Motor (counts/second)* |
| 0-5 | 0 to .25 | 0.252 | 100 |
| 5.1 to 10 | .26 to .50 | 0.1575 | 63 |
| 10.1 - 15 | .51 to .75 | 0.105 | 26 |
| 15 - 30 | .75 to 2.5 | 0.105 | 11 |

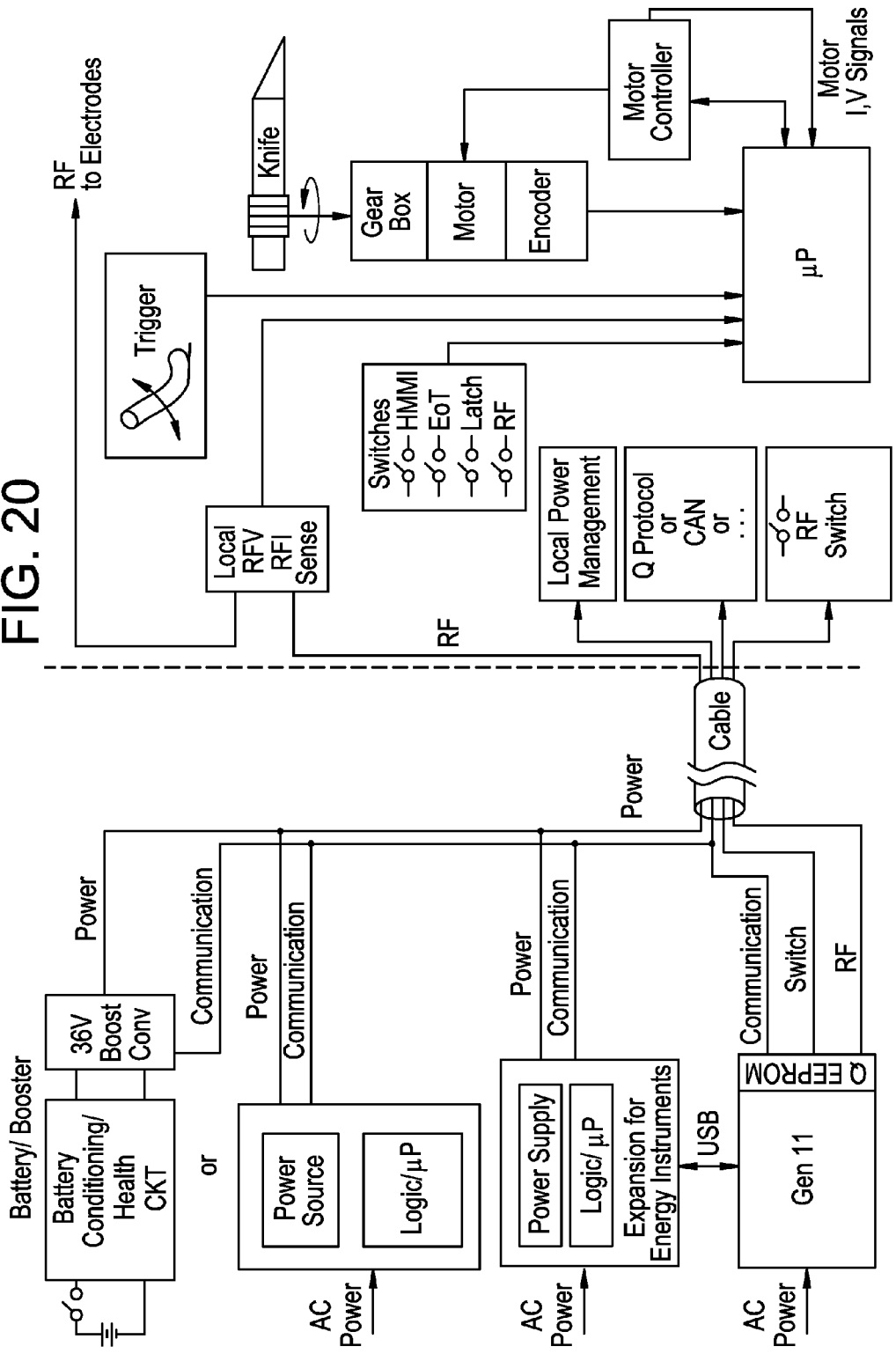

METHODS AND DEVICES FOR CONTROLLING MOTORIZED SURGICAL DEVICES

FIELD

The present invention relates to methods and devices for controlling motorized surgical devices.

BACKGROUND

Various surgical devices are used for compressing and cutting different types of tissue. In general, these devices have jaws configured to grasp tissue and a cutting mechanism configured to be advanced through the tissue to sever it. These devices can also apply energy to the tissue disposed between the jaws to promote hemostasis.

A common concern when using any of these devices is achieving hemostasis so that bleeding of the target tissue is limited. By increasing the amount of pressure applied to the target tissue, the flow of blood can be limited, decreasing the time necessary to achieve hemostasis. However, applying too much pressure too quickly to the tissue before the tissue is ready can result in trauma to the tissue, which can result in fracturing of vessels near the cut-line, potentially resulting in an elevated level of necrosis, a slower rate of healing, and/or a greater recovery period. An optimal amount of force depends on various factors, including the type of tissue, its thickness, and disease state.

Accordingly, there remains a need for improved methods and devices for controlling motorized surgical devices.

SUMMARY

A surgical device is provided that in one embodiment includes an end effector including first and second jaws configured to engage tissue between facing engagement surfaces thereof. The surgical device can also include a sensor configured to sense an impedance of the tissue engaged between the facing engagement surfaces, a cutting element configured to cut the tissue engaged between the facing engagement surfaces, a motor configured to provide an output that causes the cutting element to translate through the end effector at a speed, and a controller configured to change an output of the motor based at least in part on the sensed tissue impedance, thereby controlling the speed of the cutting element translating through the end effector.

The surgical device can vary in any number of ways. For example, the controller can be configured to change the output of the motor in real time with the cutting element translating through the end effector. For another example, the controller can be configured to prevent a velocity of the motor from exceeding a predetermined maximum threshold velocity during the translation of the cutting element through the end effector based at least in part on at least one of a current of the motor, a voltage of the motor and on revolutions per minute (RPM) of the motor, the current, the voltage, and the RPM being proportional to a load of the cutting element. For still another example, the controller can be configured to repeatedly and sequentially increase and decrease a velocity of the motor in response to the velocity of the motor reaching a predetermined threshold velocity. The repeated sequential increasing and the decreasing of the velocity can continue until the velocity of the motor falls below the predetermined threshold velocity. For yet another example, the controller can be configured to cause a feedback signal to be provided to a user. The feedback signal can be indicative of the speed of the cutting element. The feedback signal can include at least one of a light, a sound, a vibration, and a visual textual display. For another example, the surgical device can include a handle configured to be actuated by a user so as to move the first and second jaws from an open position to a closed position. The controller can be configured to prevent the translation of the cutting element through the end effector until the first and second jaws are in the closed position. For yet another example, the sensor can be disposed within a housing of the surgical device that is configured to be handheld by a user. For another example, the sensor can be remotely located from a housing of the surgical device that is configured to be handheld by a user, and the sensor can be configured to be in electronic communication with the controller from the remote location. For still another example, the controller can also be configured to change the output of the motor based at least in part on a linear force of the cutting element moving through the tissue. The controller can be configured to calculate the linear force in real time with the cutting element moving through the tissue based on one or more of the current of the motor, the voltage of the motor, the RPM of the motor, and the drivetrain of the motor. For yet another example, when the cutting element is cutting the tissue, the controller can be configured to control the output of the motor such that the output of the motor cannot exceed 80% of a total output capability of the motor, and after the cutting element has cut the tissue, the controller can be configured to control the output of the motor such that the output of the motor is allowed to exceed 80% of the total output capability of the motor. For another example, the device can include a housing having the sensor, the controller, and the motor disposed therein. For yet another example, the device can include a housing having the sensor and the controller disposed therein, and the motor can be located outside the housing and can be in electronic communication with the cutting element.

In some embodiments, the sensor can be configured to sense a reference tissue impedance of the tissue engaged between the facing engagement surfaces. When the cutting element is translating through the end effector and the sensed tissue impedance becomes greater than the reference tissue impedance, the controller can be configured to change the output of the motor so as to speed up the translation of the cutting element through the end effector. When the cutting element is translating through the end effector and the sensed tissue impedance becomes less than the reference tissue impedance, the controller can be configured to change the output of the motor so as to slow down the translation of the cutting element through the end effector.

In some embodiments, the surgical device can include a second sensor configured to sense a longitudinal position of the cutting element relative to the end effector, and the controller can be configured to change the output of the motor based at least in part on the sensed longitudinal position of the cutting element relative to the end effector. The cutting element can be configured to translate through the end effector from a start position to an end position, and the controller can be configured to change the output of the motor in response to the second sensor sensing that the cutting element translates through an intermediate position that is between the start and end positions along a longitudinal axis of the end effector.

In some embodiments, the surgical device can include a second sensor configured to sense a longitudinal position of the cutting element relative to the end effector, and the controller can configured to close the first and second jaws at a rate proportional to the sensed longitudinal position.

In another embodiment, a surgical device is provided that includes a proximal handle portion operatively coupled to a motor, a shaft extending distally from the handle portion, and an end effector at a distal end of the shaft. The end effector can be configured to engage tissue. The surgical device can also include a cutting element configured to move longitudinally through the end effector from a start position to an end position. The motor can be configured to provide power that causes the movement of the cutting element from the start position to the end position. The surgical device can also include a sensor configured to sense a position of the cutting element relative to the end effector, and a controller configured to adjust the power provided by the motor during the movement of the cutting element based at least in part on the sensed position of the cutting element relative to the end effector.

The surgical device can have any number of variations. For example, the controller can be configured to prevent the power from causing a force of the cutting element moving longitudinally through the tissue to exceed a maximum threshold amount of force in response to the sensor sensing the position of the cutting element as being at or beyond a predetermined intermediate position that is between the start and end positions. The force can be based on one or more of a current of the motor, a voltage of the motor, revolutions per minute (RPM) of the motor, and drivetrain of the motor. For another example, the controller can be configured to close the end effector at a rate proportional to the sensed position. For another example, the surgical device can include a second sensor configured to sense an impedance of the tissue engaged by the end effector. The controller can be configured to adjust the power provided by the motor during the movement of the cutting element based at least in part on the sensed tissue impedance, thereby adjusting a velocity of the cutting element moving longitudinally through the end effector.

In another embodiment, a surgical device is provided that includes a proximal portion configured to be handheld, and a distal portion including a working end configured to be advanced into a body of a patient. The working end can be configured to be movable relative to the proximal portion using electronic power supplied to the surgical device from a motor. The device can also include a cord extending from the proximal handle portion such that a free end of the cord is external to the proximal handle portion. The free end of the cord can be configured to be selectively operatively connected to and not operatively connected to a generator. The device can also include a power source configured to provide power to the motor. The power source can be external to the proximal handle portion and can be attached to the cord adjacent the free end.

The device can vary in any number of ways. For example, the power source can be removably and replaceably attached to the cord such that the power source can be detached from the cord so as to allow either the power source to be reattached thereto or for a second power source to be attached to the cord adjacent the free end. For another example, the device can include a power source housing fixedly attached to the cord adjacent the free end. The power source can be configured to be removably and replaceably disposed in the power source housing.

In another embodiment, a surgical device is provided that includes a proximal handle portion, a shaft extending distally from the handle portion, an end effector at a distal end of the shaft, the end effector being configured to engage tissue, an actuator configured to be actuated so as to cause the end effector to move relative to the shaft, and a cord extending from the proximal handle portion. The cord can be configured to operatively couple to a generator configured to provide power to the surgical device when the cord is coupled thereto. The device can also include a power source on the cord and external to the proximal handle portion.

The device can vary in any number of ways. For example, the power can be provided by the generator in response to the actuation of the actuator. The power provided by the generator can provide all the power necessary to move the end effector relative to the shaft in response to the actuation of the actuator. The power provided by the generator can provide a first partial portion of the power necessary to move the end effector relative to the shaft in response to the actuation of the actuator, a second partial portion of the power necessary to move the end effector relative to the shaft in response to the actuation of the actuator being manual power provided by a user. For another example, the power source can be removably and replaceably attachable to the cord. For yet another example, the device can include a power source housing fixedly attached to the cord, and the power source can be configured to be removably and replaceably disposed in the power source housing. For still another example, the power source can include a battery. For another example, the cord can have a first end attached to the proximal handle portion and a second end configured to removably and replaceably attach to the generator, and the power source can be on the cord proximate the second end. For still another example, the device can include a cutting element configured to move longitudinally through the end effector from a start position to an end position, and the generator can be configured to provide at least a portion of power that causes the movement of the cutting element from the start position to the end position. The device can also include a sensor configured to sense a position of the cutting element relative to the end effector. The device can also include a controller configured to adjust the power provided by the generator during the movement of the cutting element based at least in part on the sensed position of the cutting element relative to the end effector.

In another embodiment, a surgical device is provided that includes a proximal portion including a first actuator and a second actuator, an elongate shaft extending distally from the proximal portion, and first and second jaws at a distal end of the elongate shaft. The first and second jaws can be configured to clamp tissue therebetween. The device can also include an energy applicator configured to apply energy to the tissue clamped between the first and second jaws. The first actuator can be configured to be actuated so as to cause the energy applicator to apply the energy to the clamped tissue. The device can also include a cutting element configured to translate through the clamped tissue so as to cut the tissue. The second actuator can be configured to be actuated so as to simultaneously cause the energy applicator to apply the energy to the clamped tissue and the cutting element to translate through the clamped tissue so as to cut the tissue. The first actuator can be configured to be actuated so as to cause the energy applicator to apply the energy to the clamped tissue without causing the cutting element to translate through the clamped tissue so as to cut the tissue.

The device can have any number of variations. For example, each of the first and second actuators can be configured to be actuated independent of the other of the first and second actuators. For another example, the second actuator can be configured to, in response to actuation thereof, simultaneously begin causing the energy applicator to apply the energy to the clamped tissue and the cutting element to translate through the clamped tissue so as to cut the tissue. For yet another example, the second actuator can be configured to, in response to actuation thereof, begin causing the energy applicator to apply the energy to the clamped tissue in response to reaching a first predetermined threshold of actuation and causing the cutting element to translate through the clamped tissue so as to cut the tissue in response to reaching a second predetermined threshold of actuation that is after the first predetermined threshold of actuation. The first predetermined threshold of actuation can include a first amount of force applied to the first actuator and the second predetermined threshold of actuation can include a second amount of force applied to the first actuator. The second amount of force can be greater than the first amount of force. For another example, the proximal portion can include a stationary member, the first actuator can include a first movable member being actuatable by being movable relative to the stationary member, and the second actuator can include a second movable member being actuatable by being movable relative to the stationary member. The first movable member can include a button, and the second movable member can include a first movable trigger. For yet another example, each of the first and second actuators can include one of a movable trigger, a button, a lever, and a switch. For still another example, the energy can include radiofrequency energy. For another example, the device can include a third actuator configured to be actuated so as to cause at least one of the first and second jaws to move so as to clamp the tissue between the first and second jaws. The third actuator can be configured to be actuated independent of each of the first and second actuators. Each of the first and second actuators can be configured to be actuated independent of the others of the first, second, and third actuators. The third actuator can be configured to be actuated so as to cause at least one of the first and second jaws to move so as to unclamp the tissue between the first and second jaws, and the third actuator can be configured to be actuated so as to unclamp the tissue between the first and second jaws after the actuation of the first actuator so as to cause the energy applicator to apply the energy to the clamped tissue without the second actuator having been actuated. For another example, the device can include a motor configured to provide an output that drives the translation of the cutting element through the clamped tissue.

In another embodiment, a surgical device is provided that in one embodiment includes a proximal portion, an elongate shaft extending distally from the proximal portion, a working element at a distal end of the elongate shaft, the working element being configured to grasp tissue therewith, an energy applicator configured to apply energy to the tissue grasped by the working element, and a cutting element configured to move relative to the working element and cut the tissue grasped by the working element. The surgical device can have first and second modes, the first mode in which the energy is applied without the cutting element moving relative to the working element, and the second mode in which the energy is applied simultaneously with the cutting element moving relative to the working element and cutting the tissue grasped by the working element.

The device can vary in any number of ways. For example, the surgical device can have a third mode in which the working element grasps the tissue, the cutting element cuts the grasped tissue, the working element releases the cut tissue, and the energy applicator does not apply energy to the tissue before or after the tissue is cut. For another example, the device can include a motor configured to provide an output that drives the movement of the cutting element relative to the working element. For yet another example, the working element can include a pair of opposed jaws configured to grasp the tissue therebetween.

In another embodiment, a surgical device is provided that includes a proximal portion, an elongate shaft extending distally from the proximal portion, and an end effector at a distal end of the elongate shaft. The end effector can include first and second jaws configured to grasp tissue between facing engagement surfaces thereof. The end effector can be configured to move between a closed position, in which a minimum gap exists between the facing engagement surfaces when no tissue is being grasped by the end effector, and an open position in which another, larger gap exists between the facing engagement surfaces. The device can also include a first conductive member configured to directly engage the grasped tissue and apply energy to the grasped tissue, and a second conductive member configured to directly engage the grasped tissue when the first conductive member applies the energy thereto. The second conductive member can be configured to maintain the minimum gap when the first and second jaws are in the closed position.

The device can vary in any number of ways. For example, when the minimum gap exists between the facing engagement surfaces, the second conductive member can be configured to directly engage the facing engagement surface of the first jaw without directly engaging the facing engagement surface of the second jaw. For another example, the first jaw can be movable relative to the elongate shaft, to the second jaw, and to the first and second conductive members so as to move the end effector between the open and closed positions. For still another example, the first and second jaws can each be movable relative to the elongate shaft so as to move the end effector between the open and closed positions. For yet another example, the first and second conductive members can each be part of the same one of the first and second jaws. For another example, the device can include a third conductive member configured to directly engage the grasped tissue and apply energy to the grasped tissue, the first conductive member being on the facing engagement surface of the first jaw and the third conductive member being on the facing engagement surface of the second jaw. The second conductive member can be attached to the first jaw and extend from the facing engagement surface of the first jaw in a direction toward the facing engagement surface of the second jaw.

In another embodiment, a surgical device is provided that includes a proximal handle portion, an elongate shaft extending distally from the proximal handle portion, a first jaw at a distal end of the elongate shaft, the first jaw having a first tissue engagement surface, and a second jaw at the distal end of the elongate shaft. The second jaw can have a second tissue engagement surface At least one of the first and second jaws can be movable relative to the elongate shaft to facilitate clamping of tissue between the first and second tissue engagement surfaces. The device can also include a first conductive member forming at least a portion of the first tissue engagement surface. The first conductive member can be configured to apply energy to the tissue clamped between the first and second tissue engagement surfaces. The device can also include a second conductive member extending from the first tissue engagement surface in a direction toward the second tissue engagement surface. The second conductive member can be configured to contact the first tissue engagement surface so as to maintain a minimum amount of space between the first and second tissue engagement surfaces, and the second conductive member can be configured to not conduct energy when the first conductive member is applying the energy.

The device can have any number of variations. For example, the first tissue engagement surface can have a plurality of holes formed therein, and the second conductive member can include a plurality of conductive members. Each of the plurality of holes can have one of the plurality of conductive members extending therethrough. For another example, the first and second conductive members can not be in direct contact with one another. For yet another example, the device can include a third conductive member forming at least a portion of the second tissue engagement surface. The third conductive member can be configured to apply energy to the tissue clamped between the first and second tissue engagement surfaces. The second conductive member can be configured to contact the third conductive member so as to maintain the minimum amount of space between the first and second tissue engagement surfaces. For another example, the device can include a cutting element configured to translate along the first and second jaws so as to cut the tissue clamped between the first and second tissue engagement surfaces. The cutting element can be formed of a conductive material. For yet another example, the second conductive member can include a plurality of posts. For another example, material forming the second conductive member can be unitary with material forming the first jaw.

In another embodiment, a surgical device is provided that includes first and second jaws configured to grasp tissue therebetween. The first and second jaws can be configured to move between a fully closed position when no tissue is being grasped by the first and second jaws, in which facing tissue engagement surfaces of the first and second jaws are not in direct contact and in which a first non-zero distance exists between the facing engagement surfaces, and an open position when no tissue is being grasped by the first and second jaws, in which a second non-zero distance exists between the facing engagement surfaces. The second non-zero distance can be greater than the first non-zero distance. The device can also include one or more electrodes configured to apply energy to the grasped tissue, and one or more conductive spacers configured to maintain the first non-zero distance between the first and second jaws when the first and second jaws are in the fully closed position.

The device can vary in any number of ways. For example, the one or more conductive spacers can be configured to directly contact the grasped tissue when the energy is applied thereto. For another example, the one or more conductive spacers can each be spaced a distance apart from the one or more electrodes. For yet another example, the device can include a proximal handle portion, and an elongate shaft extending distally from the proximal handle portion. The first and second jaws can be attached to a distal end of the elongate shaft.

In another aspect, a surgical system is provided that in one embodiment includes a handheld surgical device that includes a proximal handle portion and a distal end effector configured to engage tissue, a motor configured to provide an output that causes the distal end effector to move relative to the proximal handle portion, a wire extending outside the proximal handle portion and being configured to be selectively attached to and detached from the motor by being reattachable thereto, and a power source attached to the wire at a location outside the proximal handle portion and being configured to provide power to the motor when the wire is attached to the motor. The power provided to the motor can allow the motor to provide the output.

The system can have any number of variations. For example, the wire can have a first end attached to the handheld surgical device and a second end configured to be selectively attached to and detached from the motor by being reattachable thereto, and the power source can be adjacent to the second end. For another example, the system can include a power source housing fixedly attached to the wire. The power source can be configured to be removably and replaceably disposed in the power source housing. For yet another example, the system can include a cutting element configured to move longitudinally through the distal end effector, and the motor can be configured to provide power that causes the movement of the cutting element. For another example, the end effector can include first and second jaws configured to move between an open position and a closed position, and the motor can be configured to provide power that causes the movement between the open and closed positions. For still another example, the motor can be located entirely outside the proximal handle portion.

In another aspect, a surgical method is provided that in one embodiment includes engaging tissue with first and second jaws of a surgical device, receiving an input from a user that causes a motor of the device to provide power that causes a cutting element to move along the first and second jaws so as to cut the engaged tissue, measuring an impedance of the engaged tissue in real time with the cutting element moving along the first and second jaws, and changing an amount of the power provided by the motor based at least in part on the measured tissue impedance.

The surgical method can vary in any number of ways. For example, the surgical method can include sensing a longitudinal position of the cutting element relative to the first and second jaws, and performing at least one of changing the amount of the power provided by the motor based at least in part on the sensed longitudinal position of the cutting element relative to the first and second jaws, and closing the first and second jaws at a rate proportional to the sensed position.

In another embodiment, a surgical method is provided that includes clamping tissue between opposed jaws at a distal end of a surgical instrument, and executing operation of the surgical instrument in one of first, second, and third modes of operation in which the surgical instrument is configured to operate. The first mode can include applying energy to the clamped tissue and then unclamping the tissue between the opposed jaws without the clamped tissue having been cut. The second mode can include applying energy to the clamped tissue, cutting the clamped tissue after the energy has been applied, and unclamping the tissue between the opposed jaws after the tissue has been cut. The third mode can include simultaneously applying energy to the clamped tissue and cutting the clamped tissue, and then unclamping the tissue between the opposed jaws.

The method can vary in any number of ways. For example, the energy can include radiofrequency energy. For another example, the second mode can also include simultaneously applying energy to the clamped tissue and cutting the clamped tissue.

BRIEF DESCRIPTION OF DRAWINGS

This invention will be more fully understood from the following detailed description taken in conjunction with the accompanying drawings, in which:

FIG. 13A is a graph showing one embodiment of cutting element velocity versus cutting element distance in length and in counts;

FIG. 13B is a graph showing maximum cutting element speed versus motor current for the embodiment of FIG. 13A;

FIG. 13C is a table showing inputs and outputs for the embodiment of FIG. 13A;

FIG. 20 is a schematic view of embodiments of power source arrangements for an embodiment of a surgical device.

DETAILED DESCRIPTION

Figure 1:
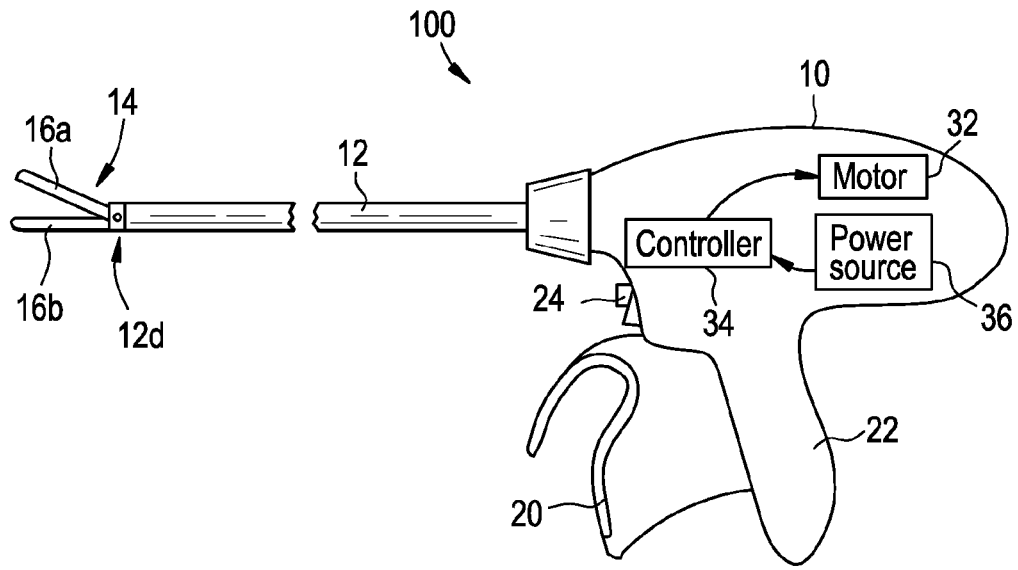
FIG. 1 is a side, partially transparent schematic view of one embodiment of a powered surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for controlling motorized surgical devices are provided. In general, the methods and devices can allow a surgical device to grasp and cut tissue. In some embodiments, the device can include at least one sensor and a motor, and an output of the motor can be configured to be adjusted based at least in part on an output from the at least one sensor. The output of the motor can be configured to provide power for translation of a cutting element along an end effector of the device. Adjusting the motor's output can cause the cutting element to translate through the end effector at different speeds, thereby allowing the cutting element to cut through tissue being grasped by the end effector at different speeds. The different speeds can facilitate the cutting of different tissues by the cutting element. Thus, thick, tough, irradiated, and/or calcified tissues can be more easily cut by the cutting element via adjustment of the motor's output. In general, motorized surgical devices can allow the application of superior compression to tissue while enabling the sealing of tough tissues, as well as delicate tissues. The device can be handheld, and the motor can be on-board the handheld device, or the motor can be external to the handheld device and be in electronic communication therewith so as to be configured to provide an output to the device from the external location. Similarly, the sensor can be on-board the handheld device, or the sensor can be external to the device and be in electronic communication therewith so as to be configured to sense parameter(s) local to the device.

FIG. 1 illustrates one embodiment of a surgical device 100 configured to grasp and cut tissue. The surgical device 100 can include a proximal handle portion 10, a shaft portion 12, and an end effector 14 configured to grasp tissue. The proximal handle portion 10 can be any type of pistol-grip or other type of handle known in the art that is configured to carry various actuators, such as actuator levers, triggers or sliders, configured to actuate the end effector 14. As in the illustrated embodiment, the proximal handle portion 10 can include a closure grip 20 and a stationary grip 22. Movement of the closure grip 20 toward and away from the stationary grip 22, such as by manual movement by a hand of a user, can adjust a position of the end effector 14. The shaft portion 12 can extend distally from the proximal handle portion 10 and can have a bore (not shown) extending therethrough. The bore can carry mechanisms for actuating the end effector 14, such as a jaw closure tube and/or a drive shaft.

As discussed further below, one or more sensors (not shown) can be coupled to the surgical device 100 and can be configured to sense data that can be used in controlling an output of the device's motor 32.

Figure 2:
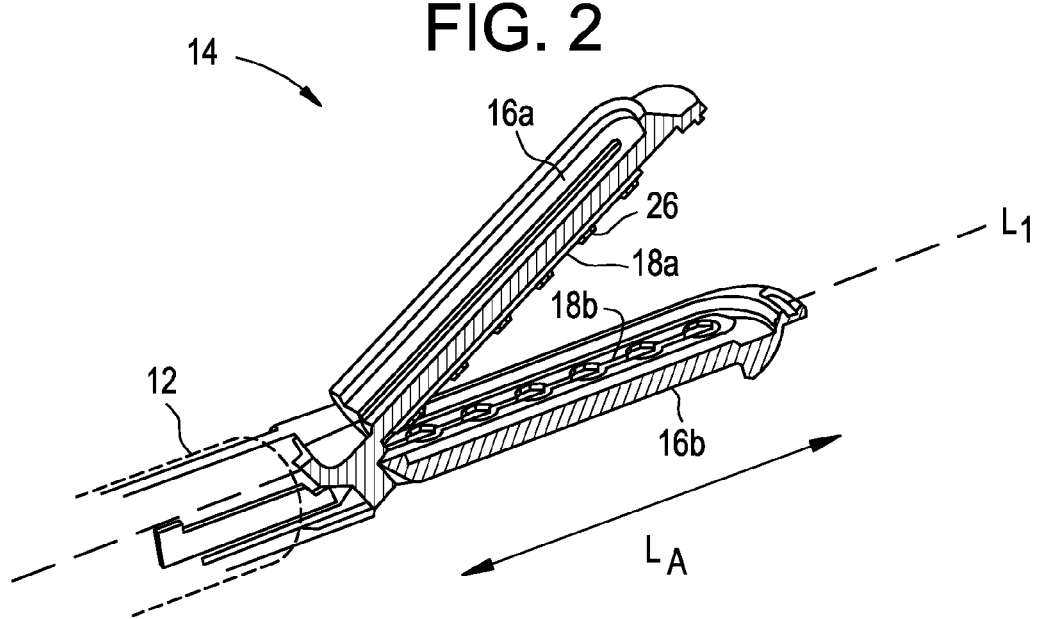
FIG. 2 is a perspective, partially transparent schematic view of a distal end of the surgical device of FIG. 1.

The end effector 14 can have a variety of sizes, shapes, and configurations. As shown in FIGS. 1 and 2, the end effector 14 can include a first, upper jaw 16a and a second, lower jaw 16b each disposed at a distal end 12d of the shaft portion 12. One or both of the upper and lower jaws 16a, 16b can be configured to close or approximate about a longitudinal axis $L_1$ of the end effector 14. Both of the jaws 16a, 16b can be moveable relative to the shaft portion 12 such that the end effector 14 can be moved between open and closed positions, or only one the upper and lower jaws 16a, 16b can be configured to move relative to the shaft portion 12 and to the other of the jaws 16a, 16b so as to move the end effector 14 between open and closed positions. When the end effector 14 is in the open position, the jaws 16a, 16b can be positioned at a distance apart from one another with space therebetween. As discussed further below, tissue can be positioned within the space between the jaws 16a, 16b. When the end effector 14 is in the closed position, a longitudinal axis of the upper jaw 16a can be substantially parallel to a longitudinal axis of the lower jaw 16b, and the jaws 16a, 16b can be moved toward one another such that the distance therebetween is less than when the end effector 14 is in the open position. In some embodiments, facing engagement surfaces 18a, 18b of the jaws 16a, 16b can be in direct contact with one another when the end effector 14 is in the closed position such that the distance between is substantially zero. In the illustrated embodiment, the upper jaw 16a is configured to pivot relative to the shaft portion 12 and relative to the lower jaw 16b while the lower jaw 16b remains stationary. In the illustrated embodiment, the jaws 16a, 16b have a substantially elongate and straight shape, but a person skilled in the art will appreciate that one or both of the jaws 16a, 16b can be curved along the longitudinal axis $L_1$ of the end effector 14. The longitudinal axis $L_1$ of the end effector 14 can be parallel to and coaxial with a longitudinal axis of the shaft portion 12 at least when the end effector 14 is in the closed configuration, and if the end effector 14 is configured to articulate relative to the shaft portion 12, when the end effector 14 is not articulated relative to the shaft portion 12.

The jaws 16a, 16b can have any suitable axial length $L_A$ for engaging tissue, where the axial length $L_A$ is measured along the longitudinal axis $L_1$ of the end effector 14, as shown in FIG. 2. The axial length $L_A$ of the jaws 16a, 16b can also be selected based on the targeted anatomical structure for transection and/or sealing. If an exemplary embodiment, the jaws 16a, 16b have a substantially equal axial length $L_A$.

The jaws 16a, 16b can have any number and any combination of features configured to facilitate grasping tissue between the facing surfaces 18a, 18b of the jaws 16a, 16b. The first and second engagement surfaces 18a, 18b can each be configured to directly contact tissue. Either one or both of the engagement surfaces 18a, 18b can include one or more surface features formed thereon that can help secure the tissue thereon. The one or more surface features can facilitate grasping of tissue, can be configured to increase friction between the tissue and the engagement surfaces 18a, 18b of the jaws 16a, 16b without tearing or otherwise damaging the tissue in contact with such surface features, and/or can facilitate forming substantially smooth, uniform layers of tissue to improve tissue effect. Examples of the surface features can include teeth, ridges, and depressions. In the illustrated embodiment, as shown in FIG. 2, the jaws 16a, 16b each include a plurality of teeth 26 positioned along an axial length of both of the engagement surfaces 18a, 18b.

One or both of the first and second jaws 16a, 16b can include one or more features configured to interact with a compression member (not shown) configured to apply compressive forces on tissue. For example, the first and second jaws 16a, 16b can include first and second recessed slots (not shown) that can receive portions of a compression member and act as a track to direct movement of the compression member. As another example, the first and second recessed slots can be configured to receive portions of a cutting element, as discussed further below.

Figure 3:
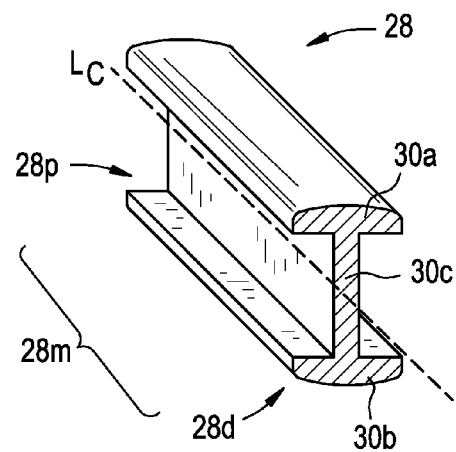
FIG. 3 is a perspective view of one embodiment of a compression member configured to translate longitudinally along an end effector.

The compression member can have various sizes, shapes, and configurations. The compression member can have an elongate shape and can be moveable proximally and distally along the longitudinal axis $L_1$ of the end effector 14. One embodiment of a compression member 28 is illustrated in FIG. 3. As shown, the compression member 28 can have a proximal end 28p, a distal end 28d, and a medial portion 28m extending therebetween. The proximal end 28p and the medial portion 28m of the compression member 28 can be sized and shaped to reciprocate within the shaft portion 12 of the device 100. The distal end 28d of the compression member 28 can be sized and shaped to interact with the jaws 16a, 16b of the end effector 14. A longitudinal axis $L_C$ of the compression member 28 can be parallel to and coaxial with the longitudinal axis $L_1$ of the end effector 14, though other configurations are possible. The compression member 28 can be actuatable from the proximal handle portion 10 of the device 100 by a first, firing actuator 24 that is operatively coupled to the proximal end 28p of the compression member 28, such as via a depressible button 24, shown in FIG. 1. Other examples of the firing actuator that can actuate the compression member include a lever, a knob, a switch, and a trigger. In general, the firing actuator 24 can be configured to be manually manipulated by a user to cause actuation of one or more other device elements, such as the compression member 28.

The compression member 28 can include a connecting portion 30c and upper and lower flanges 30a, 30b, thus providing an "I" cross-sectional shape for the compression member 28. The compression member 28 having this "I" cross-sectional shape is thus also referred to herein as an I-Blade. As in the illustrated embodiment, the upper and lower flanges 30a, 30b can be positioned substantially perpendicular to the connecting portion 30c to form the "I" cross-sectional shape. The upper and lower flanges 30a, 30b can be sized and shaped to allow the upper and lower flanges 30a, 30b to slide in the recessed slots in the upper and lower jaw 16a, 16b, respectively. This sliding contact of lateral edges of the flanges 30a, 30b and sides of each of the recessed slots can prevent lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis $L_1$ of the end effector 14.

The compression member 28 can form a distal tip of a drive shaft that moves through the end effector 14 such that only a distal portion of the drive shaft includes the compression member 28. A longitudinal length of the compression member 28 can be less than a longitudinal length of the end effector 14 such that the distal tip that includes the compression member 28 can move through the end effector 14 without the compression member 28 extending along the entire longitudinal length of the end effector 14. Alternatively, the compression member 28 can be along an entire longitudinal length of the drive shaft. The compression member 28 can thus extend along the end effector's entire longitudinal length when the compression member 28 is in its distal-most position relative to the end effector 14.

The device 100 can include a cutting element (not shown) configured to cut tissue captured between the jaws 16a, 16b. The cutting element can have various sizes, shapes, and configurations. Examples of the cutting element include a knife blade and a sharp edge. The cutting element can be sized and shaped to cut various thicknesses and types of tissue positioned between the jaws 16a, 16b of the end effector 14. In an exemplary embodiment, the cutting element can be positioned at the distal end 28d of the compression member 28, such as by being formed on the connecting portion 30c of the compression member 28 as an integral part thereof, e.g., as a sharpened edge thereof, or as a member attached thereto, e.g., a blade mounted thereon. The cutting element can have a sharp or serrated edge configured to transect tissue. In an exemplary embodiment, the cutting element can be recessed relative to distal ends of upper and lower flanges 30a, 30b of the compression member 28, which can allow compression to occur prior to the cutting element cutting tissue as the compression member 28 traverses through the jaws 16a, 16b. In another embodiment, the cutting element can be configured such that it is not attached to the compression member 28, such that the cutting element can be configured to advance and retract relative to the jaws 16a, 16b so as to cut tissue sandwiched therebetween without applying compression to the tissue. In this embodiment, the device 100 can include a separate compression member so that tissue engaged by the jaws 16a, 16b can still be compressed.

The surgical device 100 can include a second, closure actuator configured to open and close the jaws 16a, 16b of the end effector 14. Manipulation of the closure actuator, e.g., manual manipulation by a user, can cause the end effector 14 to move between the open and closed positions. In other words, manipulation of the closure actuator can cause one or both of the jaws 16a, 16b to pivot or otherwise move, as discussed above, so as to allow the jaws 16a, 16b to engage tissue, move anatomical structures, and/or perform other surgical functions. The closure actuator can have various sizes, shapes, and configurations. As in the illustrated embodiment, the closure actuator can include the closure grip 20 and the stationary grip 22. The closure grip 20 can be moveable toward and away from stationary grip 22, such as via pivoting. The closure grip 20 can have a first position in which the closure grip 20 is angularly offset from the stationary grip 22 and in which the jaws 16a, 16b are open. The closure grip 20 can have a second position that is different from the first position and in which the closure grip 20 is positioned adjacent to or substantially in contact with the stationary grip 22 and in which the jaws 16a, 16b can engage tissue and apply a force to tissue disposed therebetween. The closure grip 20 can be biased to the first position with the jaws 16a, 16b being open, as shown in FIG. 1.

The closure grip 20 can be configured to move the jaws 16a, 16b between the open and closed positions using manual or powered components. In a manually actuated embodiment, the closure grip 20 can be coupled to a gear that interacts with a rack extending in the handle portion 10, and manual movement of the closure grip 20 toward the stationary grip 22 can move the rack distally toward the end effector 14, causing a force to be exerted onto the jaws 16a, 16b to close the jaws 16a, 16b. In a powered embodiment, as shown in the illustrated embodiment of FIG. 1, the device 100 can include a motor 32, a controller 34, and a power source 36. The motor 32, the controller 34, and the power source 36 can be disposed in the proximal handle portion 10. As will be appreciated by a person skilled in the art, the motor 32 can include any type of motor (e.g., a rotary motor, etc.) configured for use with a surgical device, the controller 34 can include a variety of devices configured to process signals (e.g., a microprocessor, a central processing unit (CPU), a memory controller, etc.), and the power source 36 can include a variety of devices configured to supply power to at least the controller 34 (e.g., a battery, etc.). In some embodiments, the power source can be off-board instead of on-board the device 100, such as by the device 100 being attachable via wired connection to an electrical outlet or other power source. FIG. 20 shows embodiments of power source arrangements for an embodiment of a surgical device including a firing actuator in the form of a trigger, a cutting element in the form of a knife, a motor, a gear box, an encoder, a motor controller, a microprocessor, switches, local power management, radiofrequency electrodes, a sensor, and a cord in the form of a cable. Referring again to FIG. 1, in some embodiments, the motor can be off-board instead of on-board the device 100, such as by being attachable via a wired connection to the motor. A manual movement of the closure grip 20 can be configured to cause the controller 34 to transmit a control signal to the motor 32, which can cause the jaws 16a, 16b to close via movement of the compression member 28. The closure grip 20 can interact with one or more locking features (not shown) configured to lock the closure grip 20 relative to the stationary grip 22. For example, the one or more locking features can automatically engage when the closure grip 20 substantially contacts the stationary grip 22, or the locking feature can automatically engage at each position the closure grip 20 is pivoted through, such as via ratcheting.

The firing and closure actuators can cooperate to allow selective firing and closing of the device 100. The firing actuator 24 can be configured to be actuated to advance the cutting element through the end effector 14, apply energy to tissue, or both. Depressing or pivoting the firing actuator 25 can activate various elements in the device, and thereby cause one or more actions such as the compression member 28 and/or the cutting element advancing distally relative to the jaws 16a, 16b, and/or the compression member 28 and/or the cutting element retracting proximally relative to the jaws 16a, 16b, and/or energy being delivered to the jaws 16a, 16b. The firing actuator 24 can be in electrical communication with the motor 32. The motor 32 can be operatively coupled to the compression member 28 using, e.g., a gear and rack. As in this illustrated embodiment, activation of the motor 32 can cause advancement and/or retraction of the compression member 28.

Tissue can be difficult for the cutting element to cut, such as if the tissue is thick, tough, irradiated, and/or calcified. The tissue may thus not be able to be cut easily, or at all, if the cutting element is advanced through the jaws 16a, 16b using manual power alone, e.g., if the cutting element is advanced through the jaws 16a, 16b in response to the user's manual manipulation of a trigger handle. The motor 32 can be configured to supplement force applied by the user to the firing actuator 24 so as to facilitate cutting tissue grasped by the jaws 16a, 16b. In some embodiments, the motor 32 can provide all force used to cut tissue grasped by the jaws 16a, 16b in response to the user's actuation of an actuator such as the firing actuator 24. In this way, the tissue can be cut without the user having to uncomfortably apply force, e.g., if the user's hands are small such that the user cannot easily actuate the firing trigger 24. Even when tissue is sufficiently thin and/or tender that manual power could cut the tissue, the motor 32 providing some or all power to cut the tissue can relieve the user of strain. This can help reduce user discomfort, e.g., hand pain, that can result from repeated cutting that is performed during a single procedure and/or that is performed in a series of surgical procedures performed by the same user.

The device 100 can include at least one sensor (not shown), and the motor 32 can be configured to provide an output that is based at least in part on an output from the sensor. The controller 34 can be configured to determine an amount of power to be provided by the motor 32. The controller 34 can be configured to receive an output signal from the sensor, and based on the output signal from the sensor, cause the motor 32 to provide an output that supplies power to the cutting element. As discussed herein, the motor and the controller can not be disposed within the surgical device, e.g., need not be disposed within a handheld housing thereof. Instead, the motor and/or the controller can be located in a separate interface or within a generator to which the surgical device can be configured to operatively connect, as discussed further below.

The device 100 can be configured to provide energy, e.g., radiofrequency (RF) energy or therapeutic treatment energy, to tissue clamped between the jaws 16a, 16b. The firing actuator 24 can be configured to cause application of the energy. The energy can be applied in a variety of ways, as will be appreciated by a person skilled in the art. Examples of applying energy are described further in US Pat. Pub. No. 2012/0078139 entitled "Surgical Generator For Ultrasonic And Electrosurgical Devices" filed Oct. 3, 2011, US Pat. Pub. No. 2012/0116379 entitled "Motor Driven Electrosurgical Device With Mechanical And Electrical Feedback" filed Jun. 2, 2011, and U.S. application Ser. No. 14/166,194 entitled "Surgical Devices Having Controlled Tissue Cutting And Sealing" filed on Jan. 28, 2014, which are hereby incorporated by reference in their entireties.

As will be appreciated by a person skilled in the art, and discussed, for example, in previously mentioned US Pat. Pub. No. 2012/0078139 entitled "Surgical Generator For Ultrasonic And Electrosurgical Devices" filed Oct. 3, 2011, RF energy is a form of electrical energy that may be in the frequency range of 300 kHz to 1 MHz. The device 100 can be configured to transmit low frequency RF energy through tissue, which causes ionic agitation, or friction, in effect resistive heating, thereby increasing the temperature of the tissue. Because a sharp boundary can be created between the affected tissue and the surrounding tissue, users of the device 100, e.g., surgeons and/or other medical professionals, can operate on the tissue with a high level of precision and control, without sacrificing un-targeted adjacent tissue. The low operating temperatures of RF energy can be useful for removing, shrinking, or sculpting soft tissue while simultaneously sealing blood vessels. RF energy can work particularly well on connective tissue, which is primarily comprised of collagen and shrinks when contacted by heat. Heat generated by current flow, from the RF energy, through tissue to which the RF energy is applied can seal the tissue, e.g., form haemostatic seals within the tissue and/or between tissues, and can thus be particularly useful for sealing blood vessels, for example.

When the device 100 includes the cutting element configured to cut tissue clamped between the jaws 16a, 16b and is configured to apply energy to tissue clamped between the jaws 16a, 16b so as to seal the tissue, the device 100 can be configured to separately cut and seal tissue clamped between the jaws 16a, 16b or can be configured to simultaneously cut and seal tissue clamped between the jaws 16a, 16b.

Figure 4:
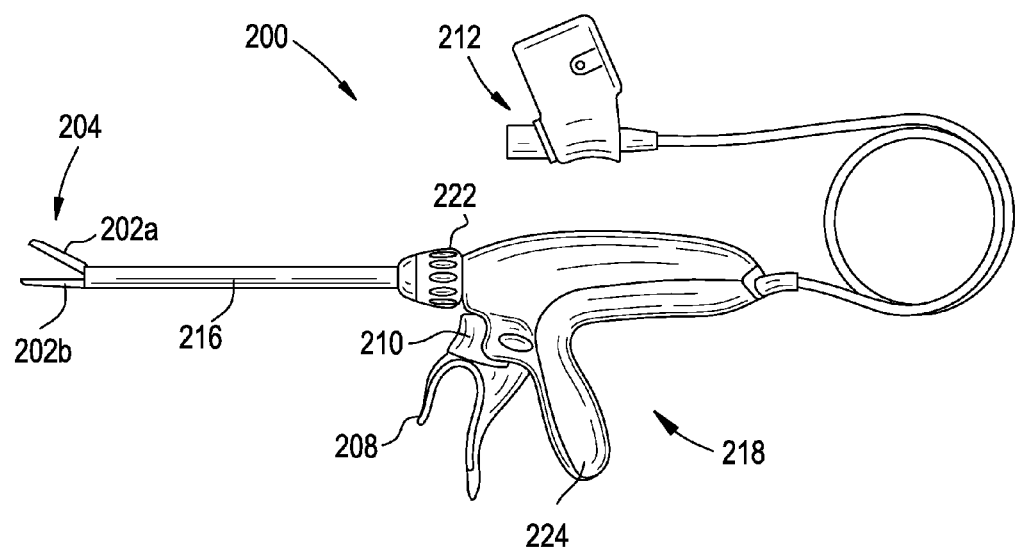
FIG. 4 is a side view of another embodiment of a powered surgical device.
Figure 5:
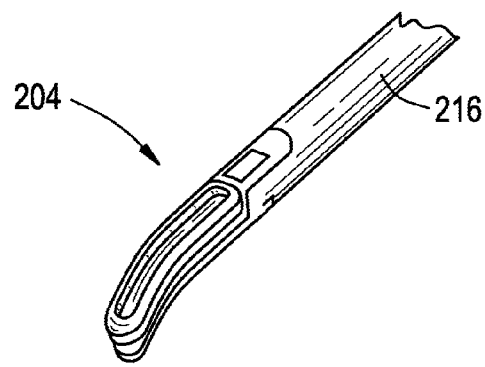
FIG. 5 is a perspective view of a distal end of the surgical device of FIG. 4.

FIG. 4 illustrates an embodiment of a surgical device 200 configured to cut and seal tissue clamped between first and second jaws 202a, 202b of the device's end effector 204. The device 200 can be configured to separately cut and seal tissue and configured to simultaneously cut and seal tissue, with a user of the device 200 being able to decide whether cutting and sealing occurs separately or simultaneously. The device 200 can generally be configured similar to the device 100 of FIG. 1. The device 200, which is also shown in FIGS. 5-9, can include a motor 206 (see FIG. 8), a closure trigger (also referred to herein as a "closure grip") 208, a firing actuator 210, a controller (not shown), a cutting element (not shown), a power connector 212 configured to attach to an external power source (not shown) such as a generator, an energy actuator 214, an elongate shaft 216 extending from a handle portion 218 of the device 200, a sensor 220 (see FIG. 8), a knob 222 configured to rotate so as to rotate the shaft 216 and the end effector 204 attached thereto about a longitudinal axis of the shaft 216, the end effector 204 at a distal end of the shaft 216, and a stationary handle 224. As shown in FIG. 5, the jaws 202a, 202b can be curved, e.g., have longitudinal axes angularly offset from the longitudinal axis of the shaft 216, which can facilitate access to and/or clamping of tissue therebetween.

In this illustrated embodiment, the sensor 220 includes a position switch, although the sensor 220 can be another type of switch, such as a Hall effect sensor, a spring pot, a potentiometer, an optical sensor, or an impedance sensor. The sensor 220 can be attached to the housing in any way, e.g., adhesive, welding, snap fits, screws, etc. The sensor 220 is shown as being disposed within the handle portion 218 of the device 200 proximate to the knob 222 in this illustrated embodiment, but the sensor 220 can be located elsewhere within the handle portion 218 or another portion of the device 200. Additionally, although only one sensor 220 is shown in this illustrated embodiment, the device 200 can include a plurality of sensors 220, which can each be the same or different type as others of the sensors 220.

Figure 6:
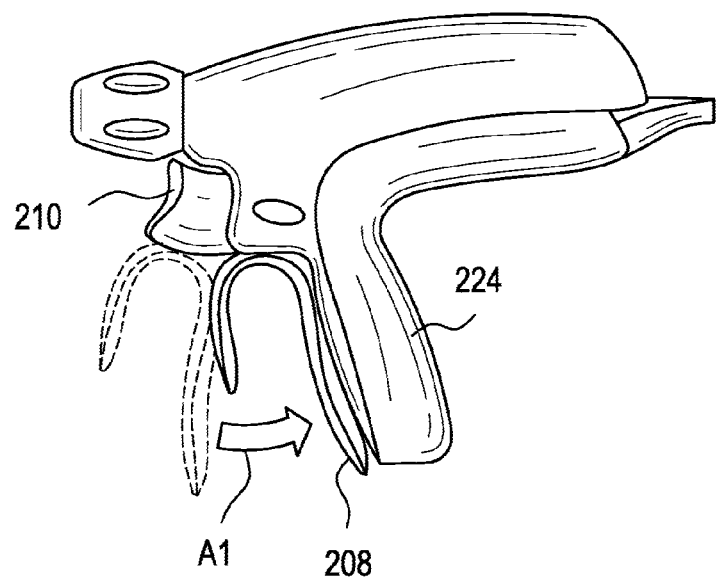
FIG. 6 is a side partial view of the surgical device of FIG. 4 showing actuation of a closure trigger of the device to move the closure trigger closed.
Figure 7:
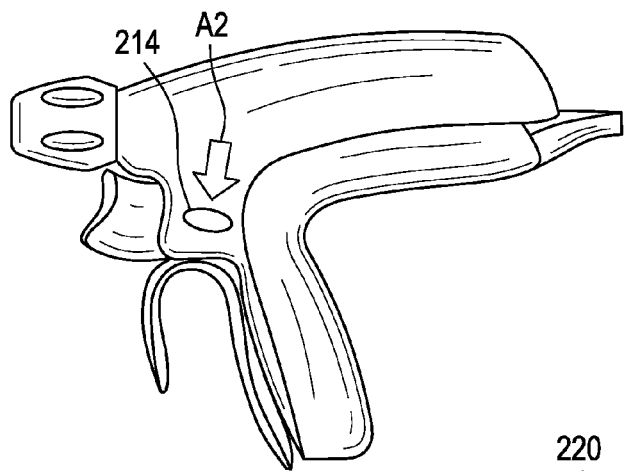
FIG. 7 is a side view of the surgical device of FIG. 6, with the closure trigger closed, showing actuation of an energy actuator of the device.
Figure 8:
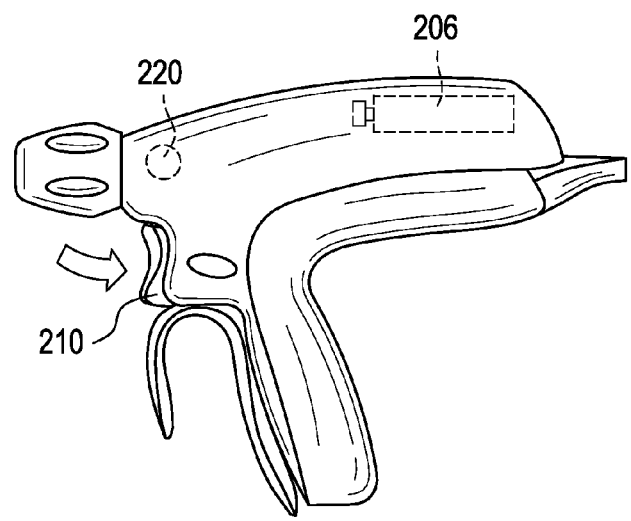
FIG. 8 is a side view of the surgical device of FIG. 6, with the closure trigger closed, showing actuation of a firing actuator of the device.
Figure 9:
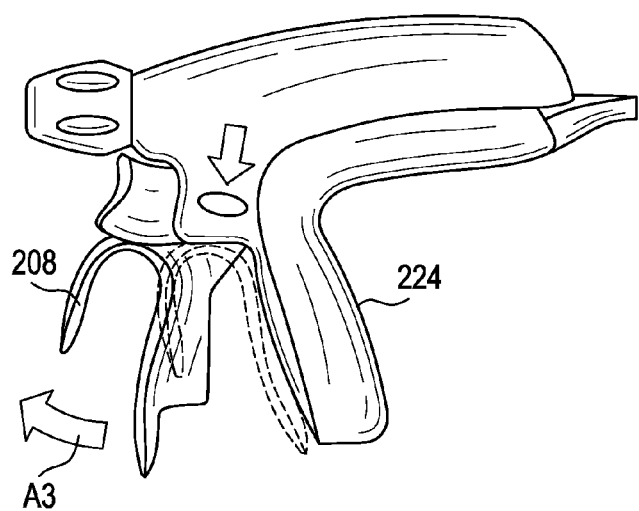
FIG. 9 is a side view of the surgical device of FIG. 6 showing actuation of the closure trigger of the device to move the closure trigger open.

As discussed further below, FIG. 4 shows the device 200 in a first position in which the motor 206 is off and in which the end effector 204 is in an open position with the jaws 202a, 202b being open with a distance of space therebetween, FIG. 6 shows the device 200 being moved to a second position from the first position in which the closure trigger 208 is being closed so as to move the end effector 206 to a closed position where the jaws 202a, 202b are closed, FIG. 7 shows the device 200 in the second position, FIG. 8 shows the device 200 being moved from the second position to a third position in which the firing actuator 210 is being actuated and the motor 206 is being turned on, and FIG. 9 shows the device 200 being moved from the third position back to the first position.

When the device 200 is in the first position, as shown in FIG. 4 and with the closure trigger 208 in shadow in FIG. 6, the closure trigger 208 is in an initial position in which the closure trigger 204 is not engaged with the sensor 220 and in which the jaws 202a, 202b are open. When the closure grip 208 is actuated, e.g., manually pulled proximally by a user's hand toward the stationary handle 224 as shown by first arrow A1 in FIG. 6, the jaws 201a, 201b can be closed so as to clamp tissue therebetween, and the closure trigger 208 can activate the sensor 220. The device 200 can be configured to lock the closure trigger 208 in the closed position, such as by including a latch (not shown) on the stationary handle 224 configured to engage the closure trigger 208 when drawn close enough thereto so as to lock the closure trigger 208 in position relative to the stationary handle 224. Alternatively or in addition, the closure trigger 208 can be manually held closed by a user. If the device 200 is not configured to lock the closure trigger 208 in a fixed position relative to the stationary handle 226, the device's sensor 220, e.g., a position sensor, can be configured to sense when the closure trigger 208 is in close proximity of the stationary handle 224, so as to indicate that the closure trigger 220 is closed.

The closure trigger 208 can activate the sensor 220 by, e.g., pushing down thereon as the closure trigger 208 is pulled toward the handle housing from which the sensor 220 can extend. If the sensor 210 is not a position switch, as mentioned above, the sensor 210 can be configured to be activated in another way, such as by being within a certain threshold distance of the closure trigger 208, as with a Hall effect sensor. Moving the closure trigger 204 can cause the jaws 208a, 208b to close, as will be appreciated by a person skilled in the art, such as by a jaw closure rod (not shown) being moved within the shaft 216. The user can "feel" the closure of the jaws 202a, 202b since the jaws 202a, 202b are being closed under manual, user power. This "feel" can allow for a better user experience by allowing the user to know that the end effector 204 is being closed, even if the end effector 204 is only partially visible or is not visible at all during end effector closure.

The activation of the sensor 220 can cause the sensor 220 to transmit a signal to the controller that indicates activation of the sensor 220. The sensor 220 being activated can indicate to the controller that the motor 206 can be turned on since the end effector 204 has been closed by actuation of the closure trigger 208.

The device 200 can be configured to prevent the energy from being applied until the sensor 220 is activated. In other words, until the sensor 220 is activated by closure of the closure trigger 208 so as to close the end effector 204, the energy cannot be activated, even if the firing actuator 210 is actuated. This can help provide safety by preventing the energy from being applied and possibly damaging material near the jaws 202a, 202b before tissue to have the energy applied thereto is clamped between the jaws 202a, 202b.

As shown in FIG. 7, the energy actuator 214 can be actuated, e.g., by being pressed by a user's finger as shown by a second arrow A2, so as to cause sealing of the tissue clamped between the jaws 202a, 202b by applying energy to the tissue. As mentioned above, the device 200 can include a safety feature that can prevent the energy from being applied until the end effector 204 is closed even if the energy actuator 214 is actuated prior to jaw closure. The controller can be configured to confirm that the sensor 220 has been activated before the energy is applied. When the controller has confirmed the activation of the sensor 210, the controller can cause the motor 202 to turn on. After the actuation of the energy actuator 214, the firing actuator 210 can be actuated, e.g., by being pressed by a user's finger as shown by a third arrow in FIG. 8, which can cause the cutting element to translate along the end effector 204 so as to cut the tissue clamped by the jaws 202a, 202b. The tissue can thus be separately sealed and cut, with the sealing occurring before the cutting. Actuation of the firing actuator 210 can be configured to cause energy to be applied, which can provide for additional sealing of the tissue during cutting of the tissue and help reduce bleeding. The tissue can thus be simultaneously cut and sealed, even if the tissue was previously sealed in response to actuation of the energy actuator 214. Alternatively, the device 200 can be configured such that only actuation of the energy actuator 214 causes application of energy, with actuation of the firing actuator 210 causing tissue cutting without causing application of energy.

If a user chooses to not actuate the energy actuator 214 prior to actuation of the firing actuator 210, and the firing actuator 210 is configured to trigger application of energy, the tissue can be sealed in response to actuation of the firing actuator 210. In this way, the tissue can be simultaneously cut and sealed. Allowing the firing actuator 210 to trigger application of energy can help ensure that the tissue is sealed, such as if the user accidentally forgets to actuate the energy actuator 214.

If the device 200 includes a compression member, which as mentioned above can have the cutting element coupled thereto, the compression member can be configured to translate along the end effector 204 in response to actuation of the firing actuator 210. Actuation of the firing actuator 210 can thus allow further closure of the end effector 204 and allow for the jaws 202a, 202b to move closer together so as to more securely grasp tissue held therebetween. The further closure of end effector 204 can help compress the tissue between the jaws 202a, 202b and allow the energy to be more pointedly directed to the tissue between the jaws 202a, 202b, can help prevent the energy from being applied to tissue before the jaws 202a, 202b have been sufficiently closed.

As shown in FIG. 9, after the tissue has been cut and sealed (separately and/or simultaneously), the closure trigger 208 can be released from its closed position so as to move back to its initial position, as shown by a third arrow A3. The closure trigger 208 can be released by being manually let go of by a user and/or by unlocking the closure trigger 208 (e.g., unlatching the latch).

In some embodiments, the device 200 can be configured to adjust an amount of power provided by the motor 206 based on an amount of pressure that a user applies to the firing actuator 210. The device 200 can be configured to detect when the user is applying a force to the actuator above a predetermined threshold of force, such as by using the sensor 220 (e.g., a Hall effect sensor, a potentiometer, etc.), thereby indicating that the tissue grasped by the end effector 204 is thick, tough, irradiated, and/or calcified, that the tissue is more difficult to cut using the cutting element. When the detected force is equal to or greater than the predetermined force, the motor 206 can be configured to provide power as a supplement the user's applied force or to provide power in place of the user's applied force. The predetermined threshold of force can be based on a human factor, e.g., how hard a human can actuate a trigger before it becomes too onerous. For example, the predetermined threshold of force can be in a range of about 2 to 4 pounds of hand grip force.

The device 200 can be configured to allow a user to manually advance the cutting element by actuating the firing actuator 210 without the motor 206 providing power for the firing. If the user applies a force less than a predetermined force, then the motor 206 can stay off. If the user applies a force equal to or greater than the predetermined force, then the motor 206 can be configured to be provide supplemental force for firing. The motor 206 can be configured to switch between providing power and not providing power based on the user's input force. The motor 206 can be configured to turn on/off without any user input other than the user's input to the firing actuator 210. The device 200 can thus be configured to provide additional force for cutting if the user is applying a certain amount of minimum force, thereby indicating that the user is having difficulty applying adequate force to the actuator 210 and/or that the tissue being cut is thick, tough, irradiated, and/or calcified. Embodiments of devices configured to allow a user to actuate an actuator without a motor providing power are described in further detail in U.S. application Ser. No. 14/166,244 entitled "Methods And Devices For Controlling Motorized Surgical Devices" filed on Jan. 28, 2014, which is hereby incorporated by reference in its entirety.

The device 200 can have a cord 211 extending therefrom. The cord 211 can have a first terminal end (not shown) disposed within the handle portion 218, e.g., within a proximal housing 213 configured to be handheld. The first terminal end can be coupled to the motor 206, which can allow power transmitted through the cord to be provided to the motor 206. The cord 211 can have a second terminal end 215 at an end of the cord 211 opposite the first terminal end. The power connector 212 can be located at the second terminal end 215, as in this illustrated embodiment.

The device 200 can also include a power source 217 attached to the cord 211 at a location external to the handle portion 218, e.g., outside the housing 213. The power source 217 in this illustrated embodiment includes a lithium battery, but another type of power source can be used. The power source 217 can be in electronic communication with one or more electronic components within the cord 211, e.g., with one or more wires therein, so as to facilitate the power source's provision of power. The power source 217 can be configured to provide power to one or more elements of the device 200, such as one or more components disposed at least partially within the housing 213, e.g., the motor 206, one or more lights, etc. The device 200 can thus have an on-board power supply, e.g., the power source 217, as well as be configured to receive external power, e.g., when the power connector 212 is plugged into a generator, an AC outlet, etc. This versatility can provide for a better user experience, as well as allow the device 200 to be used when an external power supply may not be available and/or when an on-board power supply 217 is absent or is depleted of power.

The power source 217 can be located adjacent the second terminal end 219 of the cord 211, and hence be located adjacent the power connector 212, as in this illustrated embodiment. The power source 217 being located adjacent the cord's second terminal end 219 can help the power source 217 be out of the way when the handle portion 218 is being handled since the power source 217 can be located at a remote end 219 of the cord 211 from the hand-holdable housing 213.

The device 200 can include a housing 219 attached to the cord 211 at a location external to the handle portion 218, e.g., outside the housing 213. The housing 219 can be configured to seat the power source 217 therein, which can help stably and securely attach the power source 217 to the device 200. The housing 219 can thus be located adjacent the second terminal end 219 of the cord 211, and hence be located adjacent the power connector 212, similar to that discussed above regarding the power source 217. The power source 217 can be removably and replaceably seated in the housing 219, as in this illustrated embodiment, which can facilitate recharging of the power source 217 if the power source 217 is rechargeable and/or can facilitate replacement of a spent power source 217. In other embodiments, the power source 217 can be non-removably seated within the housing 219, or non-removably attached to the cord 211 without the housing 219. The housing 219 can have a size and shape complementary to a size and shape of power sources configured to be seated therein.

Figure 10:
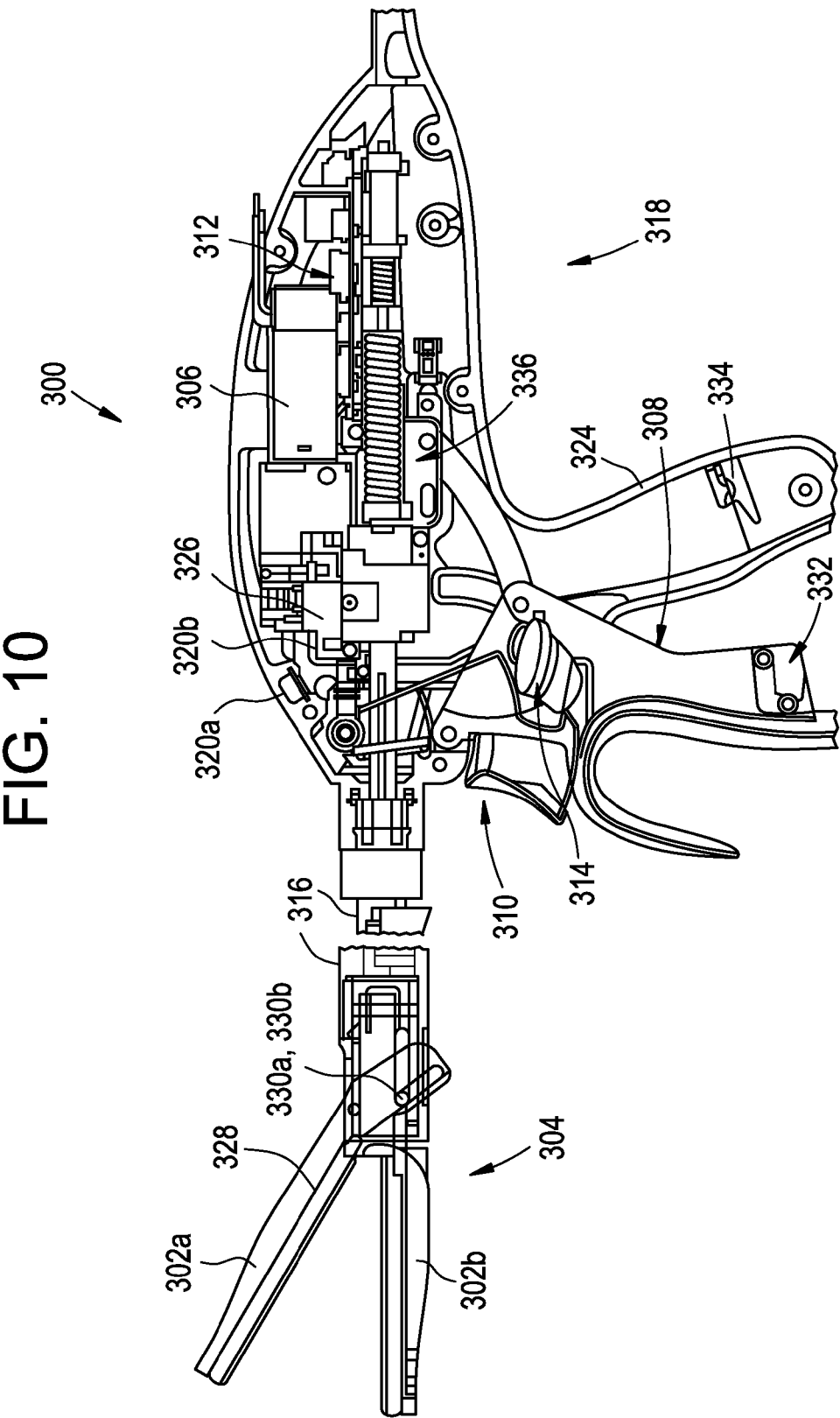
FIG. 10 is a side, partially transparent schematic view of another embodiment of a powered surgical device.

FIG. 10 illustrates another embodiment of a surgical device 300 configured to cut and seal tissue clamped between first and second jaws 302a, 302b of the device's end effector 304. The device 300 can be configured to separately cut and seal tissue and configured to simultaneously cut and seal tissue, with a user of the device 300 being able to decide whether cutting and sealing occurs separately or simultaneously. The device 300 can generally be configured similar to the device 100 of FIG. 1 and the device 200 of FIG. 4. The device 300 can include a motor 306, a closure trigger 308, a firing actuator 310, a controller 312, a cutting element (not shown), a power connector (not shown) configured to attach to an external power source (not shown), an energy actuator 314, an elongate shaft 316 extending from a handle portion 318 of the device 300, a sensor 320a, 320b, the end effector 304 at a distal end of the shaft 316, a stationary handle 324, and a gear box 326 that can be operatively connected to the motor 306 and configured to transfer output from the motor 306 to the cutting element. In this illustrated embodiment, the controller 312 includes a printed circuit board (PCB), the sensor 320a includes a Hall effect sensor, and the other sensor 320b includes a Hall effect sensor. One of the jaws 320a in this illustrated embodiment includes an insulator 328 configured to facilitate safe energy application to tissue clamped by the end effector 304. Each of the jaws 302a, 302b can include a proximal slot 330a, 330b configured to facilitate opening and closing of the end effector 304, as will be appreciated by a person skilled in the art. The device 300 can be configured to lock the closure trigger 308 in the closed position, such as by the closure trigger 308 including a latch 332 configured to engage a corresponding latch 334 on the stationary handle 324 when the closure trigger 308 is drawn close enough thereto so as to lock the closure trigger 308 in position relative to the stationary handle 324. The closure trigger latch 332 can be configured to be manually released by a user so as to unlock and release the closure trigger 308. A bias spring 336 included in the handle portion 318 can be coupled to the closure trigger 308 and cause the closure trigger 308 to open, e.g., move away from the stationary handle 324, when the closure trigger 308 is unlocked.

In some embodiments, an end effector of a surgical device, such as the device 100 of FIG. 1, the device 200 of FIG. 4, or the device 300 of FIG. 10, can be configured to prevent shorting of one or more electrodes coupled thereto and configured to facilitate sensing of parameter(s) of tissue engaged by the end effector. In this way, the device can be configured to provide reliable sensed measurements and/or to not need to be removed from within a patient during use to reset, replace and/or otherwise deal with shorted electrode(s). The end effector can be configured to prevent shorting of one or more electrodes by including one or more stop members configured to ensure that facing tissue engagement surfaces of the end effector's jaws do not contact one another when the jaws are closed. In other words, the one or more stop members can be configured to ensure that a gap of space exists between the jaws when the end effector is fully closed. In this way, one or more electrodes attached to one or both of the tissue engagement surfaces can be configured to not contact one another so as to prevent the electrode(s) from shorting.

Figure 17:
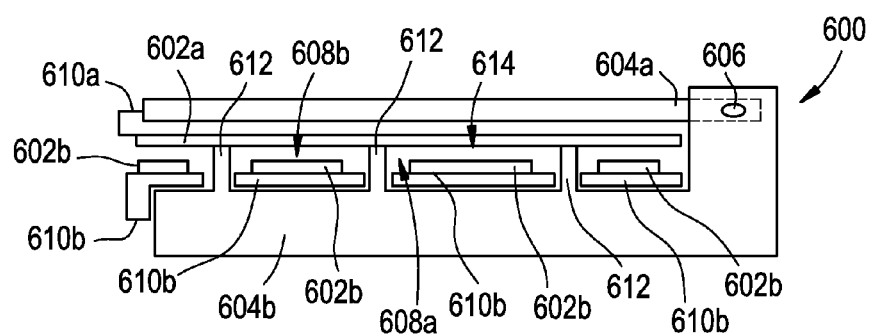
FIG. 17 is a side cross-sectional view of an embodiment of an end effector including at least one stop member.

FIG. 17 illustrates one embodiment of an end effector 600 configured to prevent shorting of one or more electrodes coupled thereto and configured to facilitate sensing parameter(s) of tissue engaged by the end effector 600. The end effector 600 can include first and second jaws 604a, 604b and can generally be configured similar to the end effectors 14, 204, 304 of the devices 100, 200, 300. In this illustrated embodiment, the first jaw 604a is pivotally attached to the second jaw 604b at a pivot point 606 about which the first jaw 604a can pivotally move relative to the second jaw 604b so as to allow the end effector 600 to open and close.

A first tissue engagement surface 608a of the first jaw 604a can include a first electrode 602a configured to contact tissue clamped between the jaws 604a, 604b. The first electrode 602a is a single electrode in this illustrated embodiment, but the first electrode can include multiple electrodes. The first jaw 604a can include a first insulator 610a positioned between the material of the first jaw 604a, e.g., stainless steel, titanium, etc., forming the first jaw 604a, and the first electrode 602a. The first insulator 610a can thus separate the first jaw 604a from the electrode 602a. In this way, when the first jaw 604a is formed of a conductive material, the first insulator 610a can prevent the electricity provided via the first electrode 602a material from also being provided via the first jaw 604a material. The first jaw 604a can thus be prevented from damaging tissue and/or other matter outside the end effector 600 when the first electrode 602a is applying energy. A second tissue engagement surface 608b of the second jaw 604b can include a second electrode 602b configured to contact tissue clamped between the jaws 604a, 604b. The second electrode 602b is in this illustrated embodiment includes multiple electrodes, but the second electrode can be a single electrode. The second jaw 604b can include a second insulator 610b positioned between the material of the second jaw 604b, e.g., stainless steel, titanium, etc., forming the second jaw 604b, and the second electrode 602b. The second insulator 610b can thus separate the second jaw 604b from the second electrode 602b. In this way, when the second jaw 604b is formed of a conductive material, the second insulator 610b can prevent the electricity provided via the second electrode 602b material from also being provided via the second jaw 604b material. The second jaw 604b can thus be prevented from damaging tissue and/or other matter outside the end effector 600 when the second electrode 602b is applying energy.

The end effector 600 can include one or more stop members 612 configured to ensure that the facing tissue engagement surfaces 608a, 608b do not contact one another when the jaws 604a, 604b are closed. The end effector 600 includes three stop members 612 in this illustrated embodiment, but the end effector 600 can include another number of stop members 612. The one or more stop members 612 can, as in this illustrated embodiment, only be attached to the second jaw 604b, e.g., a stationary one of the jaws 604a, 604b and extend toward the first jaw 604a, e.g., a movable one of the jaws 604a, 604b. In this way, the one or more stop members 612 can be less likely to snag on, damage, and/or otherwise interfere with tissue and/or other matter adjacent the end effector 600 since the stop member(s) 612 can be stationary while tissue is clamped between the tissue engagement surfaces 608a, 608b by the movable jaws 604a, 604b. In other embodiments, one or more stop members can be attached only to a movable one of the jaws, to each of an end effector's stationary and movable jaws, or to each of an end effector's two movable jaws.

The one or more stop members 612 can be connected to its associated jaw, the second jaw 604b in this illustrated embodiment, at ground. This connection can be accomplished, as in this illustrated embodiment, by the one or more stop members 612 being integrally formed with the second jaw 604b, which as mentioned above can be formed from a material such as metal.

A gap 614 of space can exist between the jaws 604a, 604b when the jaws 604a, 604b are closed, as shown in FIG. 17. The one or more stop members 612 can provide for the gap 614 by causing the first engagement surface 608a to abut thereagainst a distance away from the second engagement surface 608b. The facing first and second electrodes 602a, 602b on the first and second engagement surfaces 608a, 608b can thus be prevented from contacting one another, which can help prevent the electrodes 602a, 602b by shorting from contact thereof.

Figure 18:
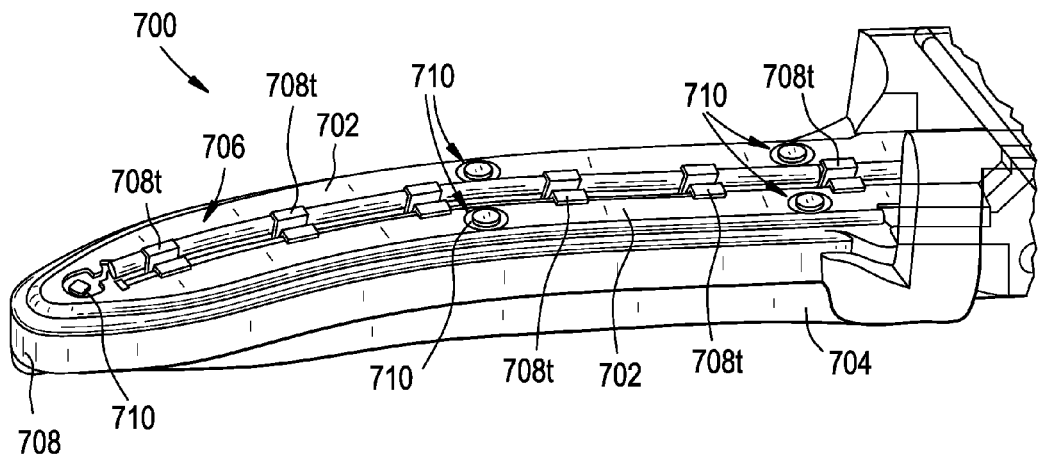
FIG. 18 is a perspective partial view of another embodiment of an end effector including at least one stop member.

FIG. 18 illustrates another embodiment of an end effector 700 configured to prevent shorting of one or more electrodes 702 coupled thereto and configured to facilitate sensing parameter(s) of tissue engaged by the end effector 700. The end effector 700 can generally be configured similar to the end effectors 14, 204, 304 of the devices 100, 200, 300. The end effector 700 can include a first, movable jaw (not shown) and a second, stationary jaw 704 similar to the first and second jaws 604a, 604b of FIG. 17.

A tissue engagement surface 706 of the second jaw 704 can include the one or more electrodes 702 configured to contact tissue clamped between the jaws. The one or more electrodes 702 in this illustrated embodiment includes a single electrode. The second jaw 704 can include an insulator 708 positioned between the material forming the second jaw 704, and the one or more electrodes 702. The tissue engagement surface 706 of the second jaw 704 can include teeth 708t of the insulator 708 thereon. The insulator 708 can separate the second jaw 704 from the second electrode 602b. In this way, when the second jaw 704 is formed of a conductive material, the second insulator 610b can prevent the electricity provided via the one or more electrodes 702 material from also being provided via the second jaw 704 material. The second jaw 704 can thus be prevented from damaging tissue and/or other matter outside the end effector 700 when the one or more electrodes 702 are applying energy, such as by preventing the second jaw 704 from being used to drill holes in tissue using energy applied therewith by pressing the second jaw 704 against the tissue.

The end effector 700 can include one or more stop members 710 configured to ensure that the facing tissue engagement surfaces of the end effector 700 do not contact one another when the end effector is closed, e.g., when the jaws are closed. The end effector 700 includes five stop members 710 in this illustrated embodiment, but the end effector 700 can include another number of stop members 710. The one or more stop members 710 in this illustrated embodiment are only attached to the second jaw 704 and extend toward the first jaw, but as discussed above, there can be any number of stop member(s), and one or both jaws of an end effector can have stop member(s) attached thereto. The end effector 700 can include the one or more stop members 710 at multiple axial positions along a longitudinal length, as in this illustrated embodiment where the end effector includes a single stop member 710 at a distal end of the end effector 700, two stop members 710 at a proximal end of the end effector 700, and two stop members 710 at an intermediate position between the proximal and distal ends of the end effector 700. Having stop members 710 at different axial positions along the end effector's longitudinal length can help ensure that the gap exists along the end effector's entire longitudinal length. The end effector 700 can, as in this illustrated embodiment, include at least one of the stop members 710 at or distally beyond a maximum distal endpoint of a cutting element's movement through the end effector 700.

Figure 19:
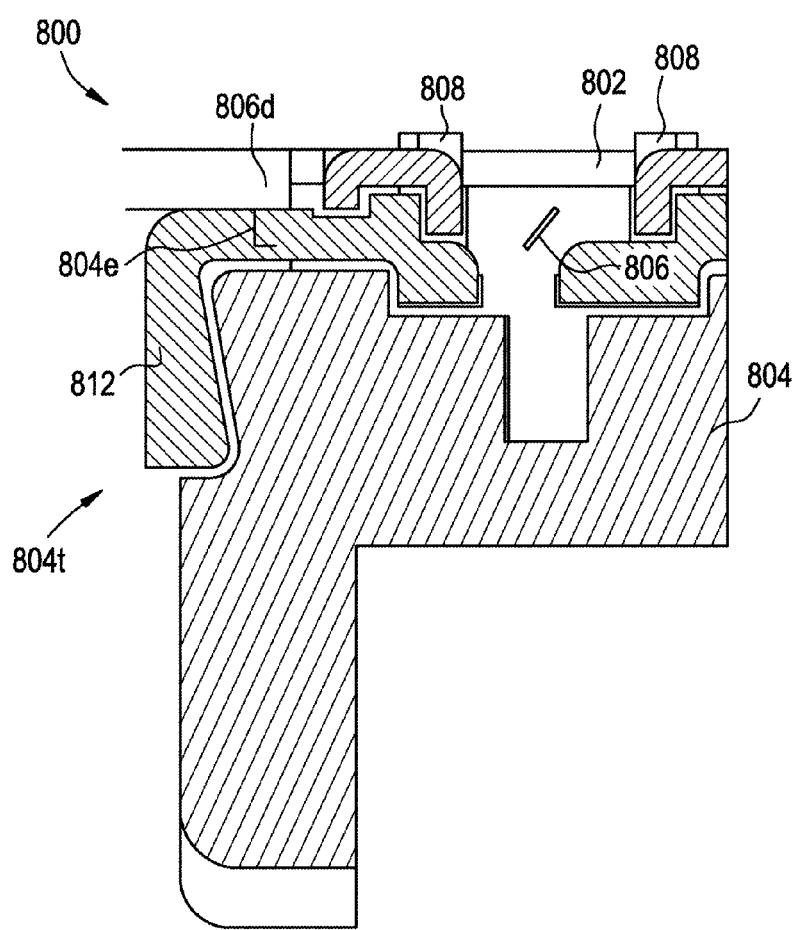
FIG. 19 is a cross-sectional view of a portion of an embodiment of a jaw of an end effector including at least one stop member.

FIG. 19 illustrates another embodiment of an end effector 800 configured to prevent shorting of one or more electrodes 802 coupled thereto and configured to facilitate sensing parameter(s) of tissue engaged by the end effector 800. The end effector 800 can generally be configured similar to the end effectors 14, 204, 304 of the devices 100, 200, 300. The end effector 800 can include a first, movable jaw (not shown) and a second, stationary jaw 804 similar to the first and second jaws 604a, 604b of FIG. 17. The end effector 800 can include one or more stop members 808.

As discussed above, the second jaws 604b, 704 of the embodiments of FIGS. 17 and 18 each have an insulator 610b, 708 separating material of the second jaws 604, 704. Conversely, the second jaw 804 of the embodiment of FIG. 19 includes an insulator 806 that does not separate material of the second jaw 804 from material of the electrode(s) 802 of the second jaw 804. The second jaw 804 can thus be configured to drill holes in tissue using energy applied therewith by pressing the second jaw 804 against the tissue. The insulator 806 can have an increased thickness in a distal area 806d thereof, which can help allow a distal tip 804t of the second jaw 804 to drill the holes. A distal edge 804e of the second jaw 804 can be moved outward to allow for the additional insulator material in the distal area 806d. The amount of movement can vary, e.g., depending on width of a cutting element that translates through the second jaw 804. For example, the amount of movement can be 0.010". Material can be removed from an area 812 at the distal tip 804t to provide extra clearance between the second jaw 804 and the insulator 806.

Figure 11:
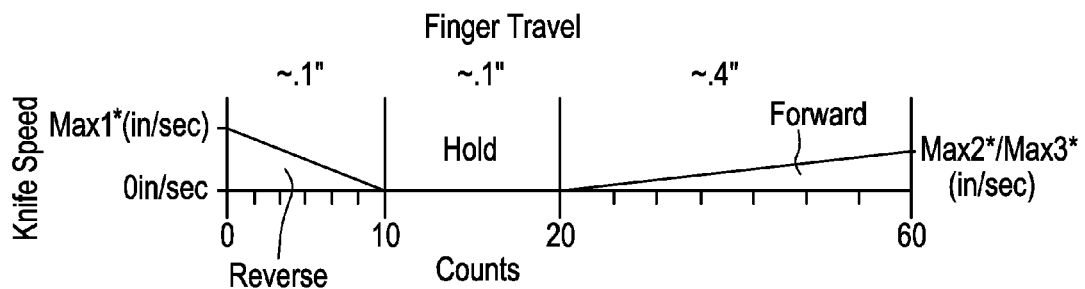
FIG. 11 is a graph showing one embodiment of a continuum of cutting element velocity versus user input and cutting element distance.

FIG. 11 illustrates a continuum of cutting element movement when a surgical device, such as the device 100 of FIG. 1, the device 200 of FIG. 4, or the device 300 of FIG. 10, is configured to adjust an amount of power provided by a motor based on an amount of pressure that a user applies to the device's firing actuator. In this illustrated embodiment, the cutting element includes a knife.

As shown in FIG. 11, A left hand edge of the continuum represents zero displacement of the firing actuator, corresponding to a zero voltage signal system input. Application of force to the firing actuator can cause increased force applied to the sensor and hence increased voltage, corresponding to a "Reverse" zone in the continuum in which first speed of the motor decreases from a first, maximum speed Max1 to a second, slower speed and the device's cutting element retracts, e.g., moves proximally. In one embodiment, the maximum speed Max1, e.g., maximum speed of cutting element reverse movement, can be 0.3 in/sec. and the second, slower speed can be 0 in/sec. If the cutting element is attached to a compression member, the compression member can retract with the cutting element. The device can include a proximally located electrical limit switch configured to signal the device's controller to stop the motor from further retracting the cutting element (and compression member, if attached thereto) when the proximal electrical limit switch is activated, e.g., when the proximal electrical limit switch closes. An amount of user input between the maximum speed Max1 and the end of the "Reverse" zone can vary. In one embodiment, the amount of user input can correspond to about 0.1 in. finger travel on the firing actuator, which can correspond to ten counts of the sensor. The maximum speed Max1 and the amount of user input can be preprogrammed into the device's controller.

Further application of force to the firing actuator can allow the cutting element (and compression member, if attached thereto) to halt retraction at any point along its stroke length. The stop is reflected by the "Hold" zone in the continuum. The stop can help prevent operator induced oscillation. An amount of user input between a start and an end of the "Hold" zone can vary. In one embodiment, the amount of user input can correspond to about 0.1 in. finger travel on the firing actuator, which can correspond to ten counts of the sensor. The amount of user input can be preprogrammed into the device's controller.

Entry into the "Hold" zone can trigger application of energy. In other words, using the embodiment shown in FIG. 11 as an example, energy application can begin at count 10. In some embodiments, the "Hold" zone can include an energy application threshold (not shown) in which energy can begin to be applied at some point after entry into the "Hold" zone, at a point after count 10 in the embodiment shown in FIG. 11. In other words, application of a predetermined threshold amount of force after the start of the "Hold" zone can cause energy to be applied to tissue being grasped by the device. This application of energy before the cutting element begins to move, e.g., before entry into the "Forward" zone, can allow the tissue to be cooked to at least some degree before cutting of the tissue begins, which can make the tissue easier to cut. The predetermined threshold amount can be a programmable variable such that it can be zeroed, e.g., entry into the "Hold" zone triggers energy application, or it can be mid-"Hold" zone, e.g., at a point after entry into the "Hold" zone. This variable can allow the energy sequence to reset during actuation of the firing actuator and this variable can be independent of a position of the cutting element relative to the end effector. This variable can thus allow energy to be reapplied without a full homing of the cutting element.

Application of additional force to the firing actuator can move into the "Forward" zone of the continuum in which the controller can cause the motor to move from a first speed to a second, maximum, faster speed Max2 in order to advance the cutting element (and compression member, if attached thereto) distally. The maximum speed Max2, e.g., maximum speed of cutting element forward movement, can be less than the maximum speed Max1, which can allow the cutting element to move faster when being retracted, e.g., when the cutting element is not cutting tissue. In one embodiment, the maximum speed Max2, e.g., maximum speed of cutting element forward movement, can be 0.25 in/sec. and the first speed can be 0 in/sec. The device can include a distally located limit switch (not shown) configured to signal the controller to stop the motor from further advancing the compression member when the distal electrical limit switch is activated, e.g., when the distal electrical limit switch closes. An amount of user input between the first speed and the end of the "Forward" zone can vary. In one embodiment, the amount of user input can correspond to about 0.4 in. finger travel on the firing actuator, which can correspond to forty counts of the sensor. The maximum speed Max2 and the amount of user input can be preprogrammed into the device's controller.

In the "Forward" and "Reverse" zones, the speed of the cutting element can be independent of a position of the cutting element relative to the tissue, and hence relative to the end effector grasping the tissue. The speed of the cutting element can be based solely upon the force applied to the firing actuator, e.g., to relative to a position of the firing actuator. In other words, the speed of the cutting element can be based upon how much a user has squeezed the firing actuator. This can help a user know how quickly the cutting element is moving by knowing how much force the user has applied to the firing actuator. In some embodiments, however, the cutting element's speed can be based upon how much force the user has applied to the firing actuator and one or more other factors, such as sensed impedance of the tissue and longitudinal position of the cutting element relative to the end effector.

The different zones of the continuum shown in FIG. 11 can allow for movement of the cutting element (and compression member, if attached thereto) proportional to a position of the firing actuator within the continuum, or the firing actuator can instead create a change in a logic state of the device such that location of the firing actuator within specific portions of the continuum, e.g., within different ones of the zones, can creates a specific change in the logic state, such as having the motor change its speed from a slow rate to a fast rate once the firing actuator reaches a specified point in the continuum, as opposed to proportional control of the motor across the entire width of the continuum. As mentioned above, the device 200 is an example of a device that can be operated over the continuum, such as the sensor 220 being configured to provide a signal to the controller that the controller can use to control the motor 206 according to the continuum of FIG. 11.

The continuum can include a "Dead Band" zone (not shown) at a leftmost end thereof, e.g., to the left of the "Reverse" zone. The "Dead Band" zone can correspond to a low level of input force. The "Dead Band" zone can accommodate minor sensor drift from the initial zero value during device operation.

Figure 12:
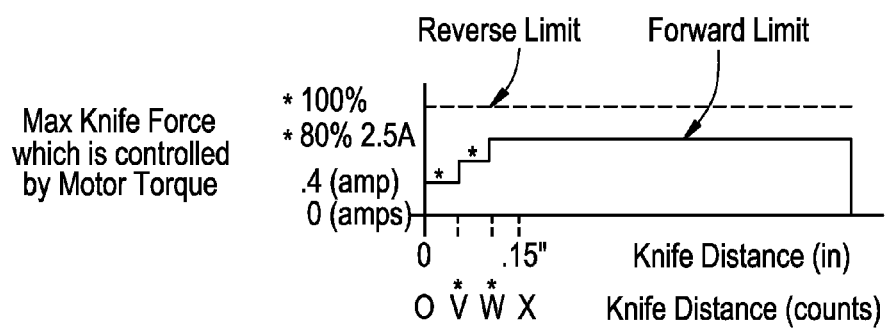
FIG. 12 is a graph showing one embodiment of maximum cutting element force versus cutting element distance in length and in counts.

FIGS. 12-13C illustrate embodiments of knife output response for the proportional control input represented by the continuum of FIG. 11. As shown in FIG. 12, power provided by the motor can be controlled based on a position of the cutting element, e.g., knife, on the end effector through which the cutting element is configured to translate. In other words, an output of the motor can be adjusted based on the position of the cutting element relative to the end effector. A speed of the cutting element can thus be controlled based on the cutting element's position on the end effector since the motor's output can include power that causes the cutting element to translate along the end effector. The speed of the cutting element through tissue clamped by the end effector can thus reflect how much of the tissue has already been cut. The position of the cutting element that can be used in determining motor speed, and hence in determining cutting element speed, can be a longitudinal position of the cutting element along a longitudinal length of the end effector that extends between a start position of the cutting element, e.g., a proximal-most position of the cutting element prior to the cutting element cutting tissue clamped between the jaws, and an end position of the cutting element, e.g., a distal-most position of the cutting element after the cutting element has cut tissue clamped between the jaws.

The position of the cutting element on the end effector can be determined in a variety of ways. For example, the device can include a first sensor at a handle portion thereof and a second sensor at the cutting element. The first sensor can be a reference sensor with which a position of the second sensor can be compared, e.g., by a controller of the device. The location of the second sensor relative to the first sensor can indicate the cutting element's position relative to the end effector. In other words, a greater a distance between the first and second sensors, the farther the cutting element has translated distally or forward along the end effector. For another example, the device can include a first, reference sensor at a stationary one of two jaws thereof and a second sensor at the cutting element.

The output of the motor can have a maximum limit. The maximum limit can be different in the "Reverse" zone than in the "Forward" zone, which can reflect that it can be harder for the cutting element to move forward since it can cut tissue while moving forward. As shown in FIG. 12, a maximum Reverse limit for when the device is operating in the "Reverse" zone can correspond to 100% of a maximum cutting element force which is controlled by motor torque, e.g., by the motor's output. A maximum Forward limit for when the device is operating in the "Forward" zone can be less than the maximum Reverse limit. In the illustrated embodiment, the maximum Forward limit is 80% of the maximum Reverse limit, e.g., 80% of the maximum cutting element force which is controlled by motor torque. The value of the maximum Forward limit is 2.5 A in this illustrated embodiment, but that value can vary based on one or more factors, e.g., type of motor, size of end effector, size of cutting element, etc. The device can be configured to prevent the motor from providing an output above the maximum Forward limit when the device is operating in the "Forward" zone, thereby helping to prevent the motor from stalling. In this way, if a user applies a relatively large amount of force to the firing actuator, such as if the user is particularly forceful, if the user uses two hands instead of one hand to apply force, and/or if the user believes that the cutting element is having difficulty cutting through tissue, the device can help prevent the motor from increasing its output beyond safe operating limits of the motor. The device (e.g., the device 100 of FIG. 1, the device 200 of FIG. 4, and the device of FIG. 10) can be configured to be held in one hand and have its closure trigger, firing actuator, and energy actuator all actuated by that same hand, which can help make the device easy to use and/or allow the user's other hand to attend to other matters during surgery. Thus, if two hands are used to apply force to the device, the force may be too much for the motor, but the device can be configured to address such a scenario as discussed herein.

The maximum limit of the motor's output can based on the cutting element's position relative to the end effector. The maximum Forward limit can define an overall maximum for the motor's output when the cutting element is moving forward. The device can be configured to have one or more lower maximum Forward limits that depend on the cutting element's position on the end effector. In this illustrated embodiment, the device is configured to include a first lower maximum Forward Limit for when the cutting element is located between its initial, zero position and a first distance V, a second lower maximum Forward Limit, that is higher than the first lower maximum limit and lower than the overall maximum Forward Limit, for when the cutting element is located between the first distance V and a second distance W, and the overall maximum Forward limit for when the cutting element is between the second distance W and a maximum distance Y. The first and second distances V, W can vary based on any one or more factors, e.g., type of motor, size of end effector, size of cutting element, etc. In this illustrated embodiment, the first lower maximum Forward Limit is 0.4 A, the first distance V is 0.05 in, the second distance is 0.1 in., and the maximum distance Y of the cutting element from the zero position is 1.29 in. Thus, in this embodiment, 0 in. represents the cutting element's start position, and 1.29 in. represents the cutting element's end position. Table 1 illustrates an embodiment of cutting element distances and maximum allowable cutting element force (lbf).

TABLE 1

| Cutting Element Stroke Distance (in) | Max Allowable Cutting Element Force (lbf) |
| --- | --- |
| 0 | 20 |
| 0.05 | 20 |
| 0.1 | 30 |
| 0.25 | 50 |
| 1.26 | 50 |

In response to reaching the overall maximum Forward limit, the device, e.g., the controller, can be configured to provide a stall alert to a user of the device. The user can thus be made aware that the motor is approaching its maximum amount of force and that, in order to avoid a motor stall, the user should not apply additional input to the firing actuator and/or should reduce an amount of force being applied to the firing actuator. The overall maximum Forward limit being less than the Reverse limit, which as mentioned above can be 100% output, can allow the overall maximum Forward limit to serve as a predetermined threshold for a stall condition since the overall maximum Forward limit can be below the 100% output level of the motor. The stall alert can have a variety of forms. For example, the stall alert can include the motor repeatedly and sequentially increasing and decreasing in velocity. This repeated back and forth can cause the device to palpably shake, thereby allowing a user holding the device to feel the shaking and hence receive the stall alert. The repeated sequential increasing and the decreasing of the velocity can continue until the motor output falls below the maximum limit. The controller can be configured to cause this repeated increase/decrease in motor output. For another example, the stall alert can include illuminating one or more lights on the device. For yet another example, the stall alert can include sounding one or more tones, such as through a speaker in electronic communication with the device. For another example, the stall alert can include providing a textual message on a display screen coupled to the device.

As shown in FIG. 13A, absolute maximum speed of the cutting element, e.g., knife, can be based on the cutting element's position relative to the end effector. In a first region A between the cutting element's initial, zero position and a third distance X greater than the second distance W, the cutting element can have a first maximum forward speed Max3. In a second region B between the third distance X and the maximum distance Y, the cutting element can have a second maximum forward speed Max2. The first and second maximum forward speeds Max2, Max3 are also shown in FIGS. 11, 13B, and 13C. The cutting element having a first maximum speed Max3 during its initial forward translation through the end effector that is less than a subsequent maximum speed Max2 reflects that, as discussed above, tissue can become easier to cut after application of heat thereto, e.g., after energy has been applied thereto, so the cutting element can move faster therethrough to effectively cut the tissue. The first maximum forward speed Max3 can help accommodate for a situation such as the end effector being fully stuffed with tissue and the user inputting a force for full speed of the cutting element. Preventing the cutting element from reaching the full speed by limiting the speed to the first maximum forward speed Max3, until region B is reached, can help prevent the cutting element (and compression member, if the cutting element is attached thereto) from jamming in the jaws.

FIG. 13B illustrates the maximum speed Max2 or Max3 of the cutting element, e.g., knife, as represented by motor counts per second versus knife load as represented by motor current. As demonstrated by FIG. 13B, if the cutting element encounters tissue during its forward translation therethrough that increases the load on the motor beyond certain thresholds, the maximum speed (Max2/Max3) of the motor can be reduced. The load of the motor can be reduced as shown in the table of FIG. 13C. The numerical values in the table of FIG. 12C are representative of the illustrated embodiment. The numerical values can be different in other embodiments based on one or more factors, e.g., type of motor, size of end effector, size of cutting element, etc. FIGS. 13B and 13C illustrate that cutting element speed can be based on motor torque independent of the cutting element's position on the end effector. In other words, if speed decreases due to cutting element load, the speed will remain decreased, at least until the cutting element load becomes less. FIGS. 12 and 13C illustrate that motor torque can be based on position of the cutting element relative to the end effector. FIGS. 13A and 13C illustrate that cutting element speed can be limited by position of the cutting element relative to the end effector.

Table 2 shows cutting element load being proportional to motor torque, e.g., to motor current using the values and limits of FIG. 13C. As mentioned above, the device's controller can be preprogrammed with these cutting element speed limits.

TABLE 2

| Dynamic Response Variable Cutting Element Load (lbf) | User Input Target Time (seconds) | Calculated Max. Speed Max. Cutting Element Velocity (in/sec) |
| --- | --- | --- |
| 0 | 5 | 0.252 |
| 10 | 8 | 0.1575 |
| 20 | 12 | 0.105 |
| 40 | 12 | 0.105 |
| 60 | 12 | 0.105 |
| 90 | 12 | 0.105 |

Figure 14:
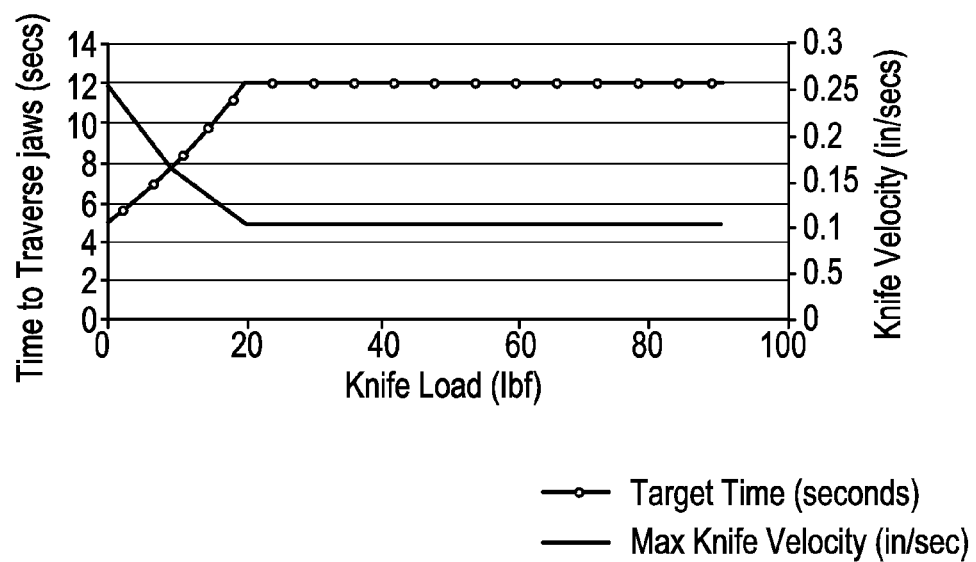
FIG. 14 is a graph showing one embodiment of time for a cutting element to traverse jaws of a powered surgical device versus cutting element load.

FIG. 14 shows a time for the cutting element of Table 2 and FIGS. 12-13C to traverse the jaws of the end effector versus the load of the cutting element, which in this embodiment includes a knife.

In some embodiments, the device, e.g., the device 100 of FIG. 1, the device 200 of FIG. 4, or the device 300 of FIG. 10, can include a motor, a cutting element, and a sensor configured to sense an impedance of tissue engaged by the device, e.g., tissue clamped by an end effector of the device. The motor's output can be based at least in part on the sensed impedance, thereby allowing speed of the cutting element through the clamped tissue to be based at least in part on the impedance of the tissue being cut. When energy is applied to tissue, such as during the sealing of tissue, water is driven out of the tissue as the tissue is heated or "cooked." Less water in the tissue causes the impedance of the tissue to decrease, e.g., from an initial impedance in a range of about 25 to 30Ω before application of energy to a range of about 3 to 4Ω during energy application. Thus, a decrease in the tissue's impedance can indicate that is having energy applied thereto. Similarly, the more the tissue's impedance decreases, the more energy the tissue can be presumed to have had applied thereto. When the tissue has become heated or "cooked," the impedance can begin to rise, e.g., to a range of about 300 to 400Ω. The sensor sensing the tissue's impedance can thus provide an indication as to whether or not the tissue is having energy applied thereto and/or as to an amount of energy that has been applied to the tissue. The output of the sensor that indicates the tissue's impedance can be used in controlling the motor's output so as to drive the cutting element faster or slower through the tissue based on the sensed impedance. In general, when the sensed impedance is low, the motor's output can be low so as to move the cutting element at a relatively slow speed since the impedance indicates that the tissue is not yet heated or "cooked." When the sensed impedance increases, the motor's output can be increased so as to speed up the cutting element's translation through the tissue since the higher impedance can indicate that the tissue has lost water due to energy application and has hence become tougher to cut, thereby likely benefitting from an increase in cutting element speed. Using impedance in controlling the motor's output, and hence in controlling the cutting element's cutting speed, can be a control transparent to a user of the device, thereby facilitating usability of the device since the user need not make any manual adjustments of the device while the tissue is being cut to facilitate efficient cutting of the tissue.

Figure 15:
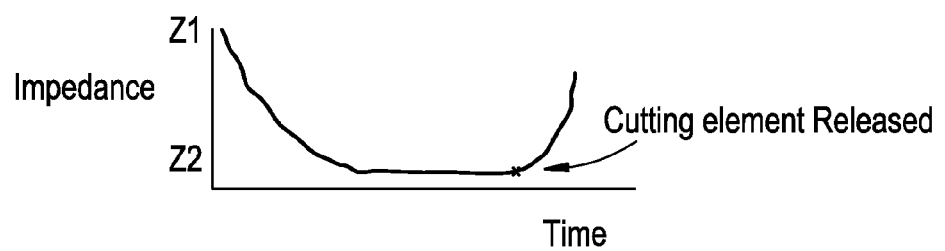
FIG. 15 is a graph showing one embodiment of tissue impedance versus time for a powered surgical device.
Figure 16A:
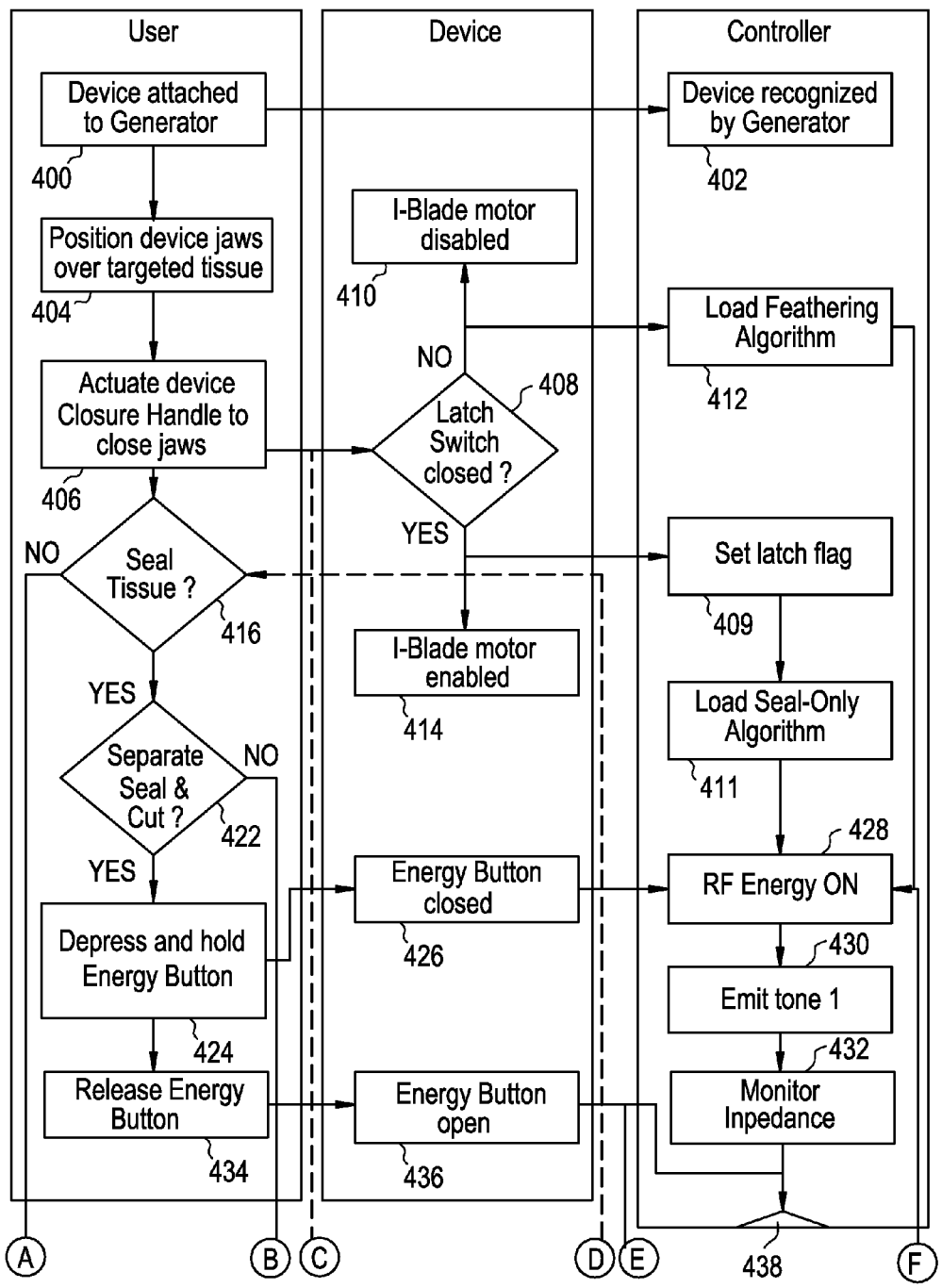
FIG. 16A is a flowchart showing one embodiment of a surgical method using a powered surgical device.
Figure 16B:
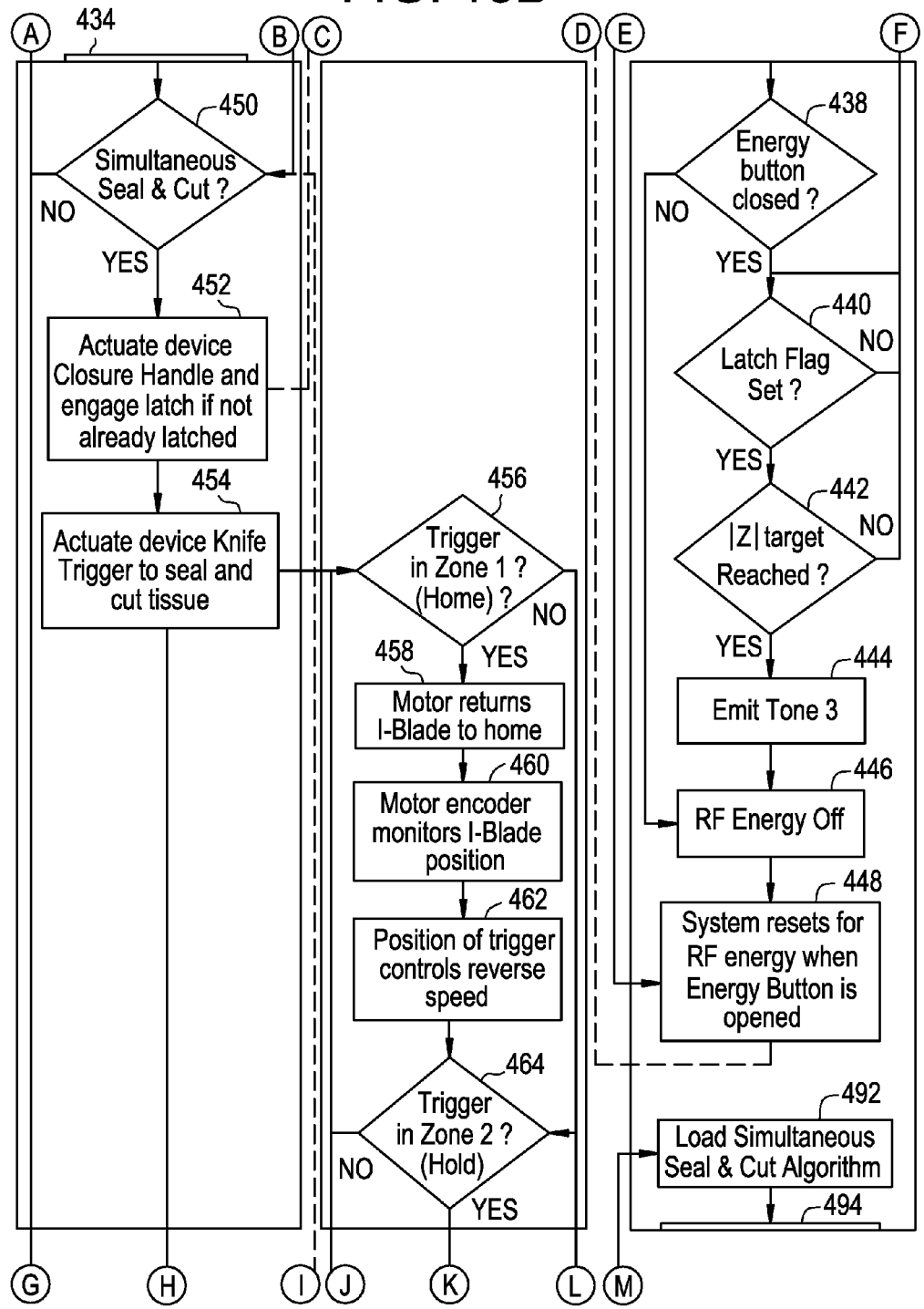
FIG. 16B is a continuation of the flowchart of FIG. 16A.
Figure 16C:
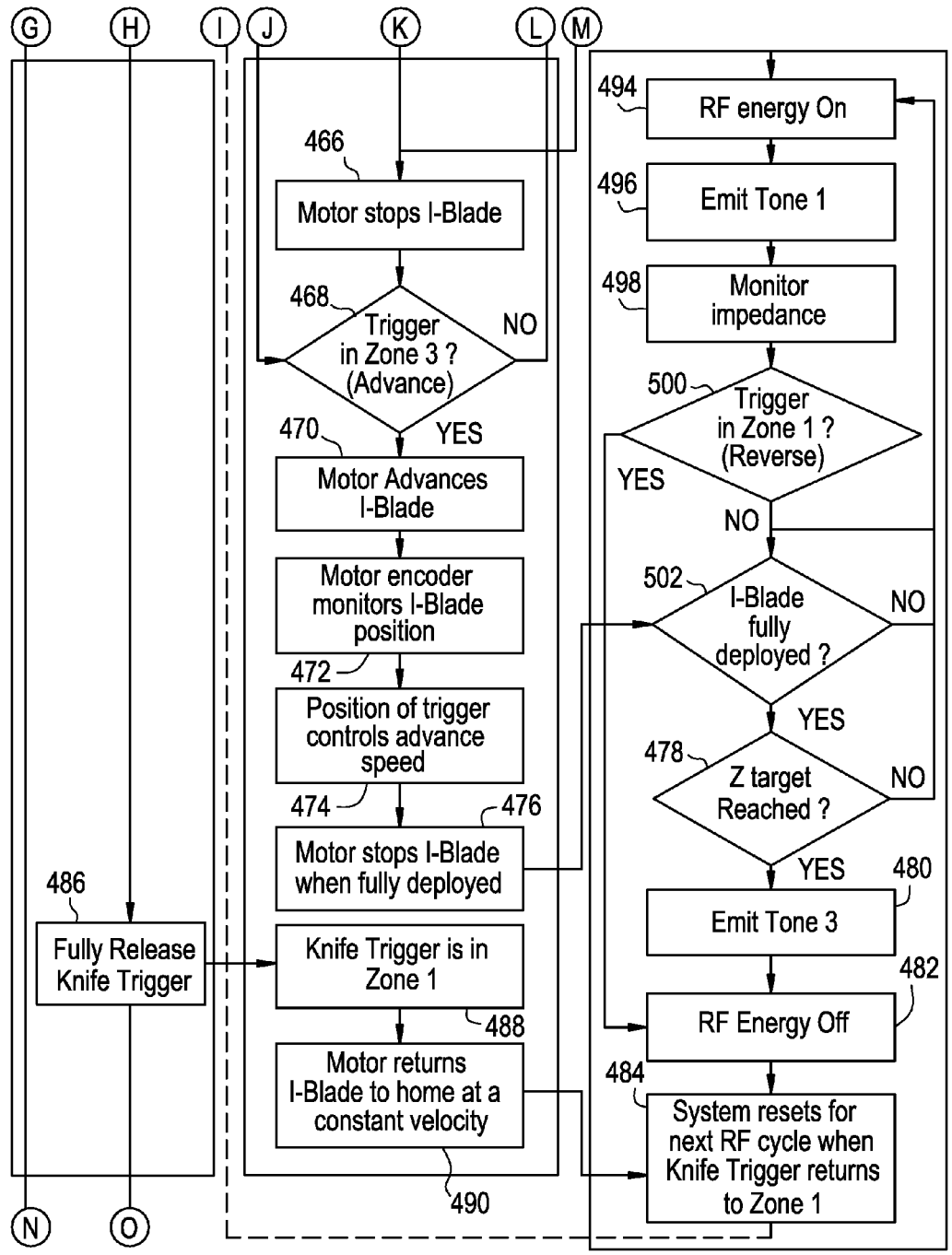
FIG. 16C is a continuation of the flowchart of FIG. 16B.
Figure 16D:
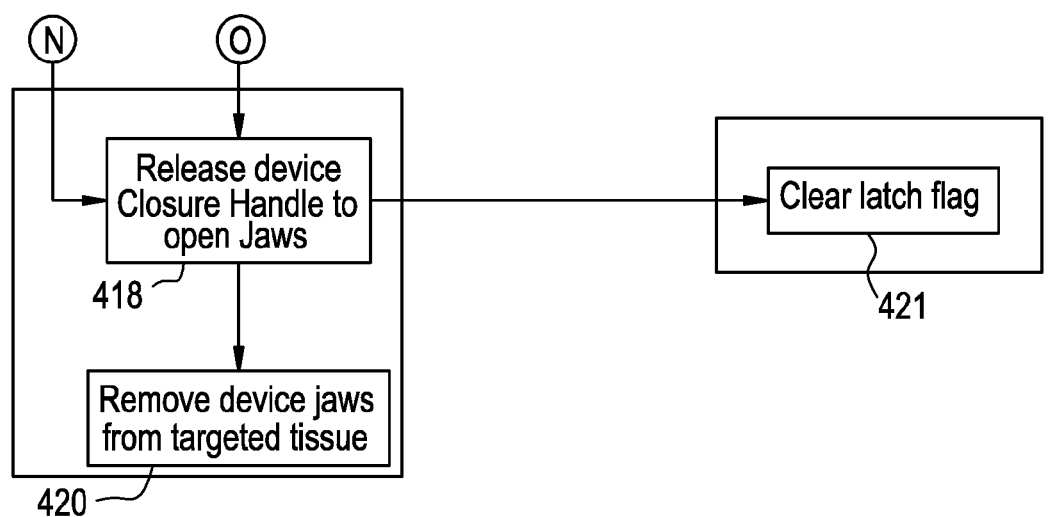
FIG. 16D is a continuation of the flowchart of FIG. 16C.

FIG. 15 illustrates an example of tissue impedance changing during energy application to the tissue and cutting element movement based on the impedance. Energy can be applied to tissue having an initial impedance Z1, e.g., in a range of about 25 to 30Ω. The energy application can cause the impedance to decrease down to a lower impedance Z2, e.g., in a range of about 3 to 4Ω. After the impedance has been sensed at the lower impedance Z2 for a threshold amount of time, the lower impedance Z2 can be presumed to indicate the heating or "cooking" of the tissue such that the cutting element can be released for movement through the tissue. The impedance can then increase from the lower impedance Z2 as the tissue is cut by the cutting element. Although not shown in FIG. 15, the impedance can increase higher than the initial impedance Z1, e.g., to a range of about 300 to 400Ω.

The sensor that senses the impedance can be attached to, for example, one of the jaws, e.g., on a tissue engagement surface thereof, so as to be in direct contact with tissue clamped between the jaws. If the device includes multiple sensors configured to sense impedance of tissue clamped by the end effector, each of the jaws can include one or more sensors configured to be in direct contact with tissue clamped between the jaws.

Table 3 illustrates an embodiment of sensed tissue impedance and maximum cutting element speeds. In other words, in the embodiment of Table 3, when the sensed impedance is equal to or greater than zero Ω and equal to or less than 10Ω a speed of the cutting element can be controlled to have a maximum speed of zero in/sec, e.g., a controller can control the speed to not exceed zero in/sec. The other sensed impedances and maximum cutting element speeds shown in Table 3 can be similarly controlled, e.g., when the sensed impedance is greater than 10Ω and equal to or less than 20Ω, the speed of the cutting element can be controlled to have a maximum speed of 0.1 in/sec, e.g., the controller can control the speed to not exceed 0.1 in/sec.

TABLE 3

| Tissue Impedance (Z) (Ohms) | Maximum Cutting Element Speed (in/sec) |
| --- | --- |
| 0 ≤ Z ≤ 10 | 0 |
| 10 < Z ≤ 20 | 0.1 |
| 20 < Z ≤ 50 | 0.15 |
| 50 < Z ≤ 100 | 0.6 |
| 100 < Z ≤ 1000 | 1.35 |

The surgical devices disclosed herein, e.g., the device 100 of FIG. 1, the device 200 of FIG. 4, and the device 300 of FIG. 10, can be used to perform a surgical procedure in which tissue is grasped and transected. The tissue can include, for example, stomach tissue, intestinal tissue, esophageal tissue, or blood vessels. The surgical procedure can be a minimally invasive procedure or an open surgical procedure. The surgical devices disclosed herein can be used in robotic-assisted minimally invasive or open surgical procedures.

For example, a minimally invasive surgical procedure can begin by preparing the patient for surgery and making one or more appropriately sized incisions at a desired location. In a minimally invasive procedure, one or more cannulas or trocars can be positioned in the incision(s) to provide access to the surgical site. One or more viewing devices, e.g., scopes, can be placed in one of the incisions to allow medical personnel to view the surgical site from outside the body. Once the patient is prepared for surgery, a surgical device can be inserted through an incision and/or through a cannula, and an end effector of the surgical device can be positioned adjacent to a desired tissue to be treated. As the surgical device is being inserted into the patient, a closure grip of the surgical device can be disposed adjacent to a stationary handle of the surgical device so that the end effector is in a closed position and occupies a smaller amount of space than when in an open position. When the end effector is positioned adjacent to the tissue to be treated, the closure grip can be moved away from the stationary grip, and the tissue to be treated can be positioned between facing engagement surfaces of the end effector's jaws. Movement of the closure grip toward the stationary handle can close the jaws so that the engagement surfaces are in direct contact with the tissue and so that the tissue is securely grasped between the jaws. A position of the jaws can directly correspond to a position of the closure grip relative to the stationary grip. With the jaws having tissue grasped therebetween, a user can engage a firing actuator which can advance a cutting element to cut the grasped tissue and/or a compression member to further compress the grasped tissue. In another embodiment, the device can automatically cause a cutting element and/or a compression member to advance through the jaws. A person skilled in the art will appreciate that, optionally, energy can be applied to the tissue prior to or during transection of the tissue between the jaws, such as by actuating an energy actuator. After the cutting element is advanced through the tissue and is refracted proximally, the device can continue to apply energy to the cut tissue or the jaws can automatically release the tissue.

FIGS. 16A-16D illustrate an embodiment of a method of using a surgical device to cut and seal tissue in a surgical procedure. The method is described with respect to the device 200 of FIG. 4, but any of the devices disclosed herein, e.g., the device 100 of FIG. 1 and the device 300 of FIG. 10, can be used in the method of FIGS. 16A-16D discussed further below. FIGS. 16A-16D show aspects of the method performed by a user (left column), by a device (middle column), and by a controller of the device (right column). Actions shown in FIGS. 16A-16D in rectangles are actions performed by the user, device, or controller, while actions shown in triangles are decisions that can determine subsequent actions performed, as discussed further below.

The user can attach 400 the device 200 to a power source using the power connector 212. For example, the power connector 212 can be plugged into a generator. The generator can be configured to recognize the device 200 as an acceptable input thereto and transmit a signal to the device 200 indicating that the device 200 has been properly connected to and recognized by the generator. The device's controller can receive 402 the signal indicating the recognition. The device 200 being recognized by the generator can trigger initial homing and calibration of the sensor 220, e.g., sensing an initial home position of the cutting element, etc.

The user can insert the end effector 204 into a patient, e.g., through a trocar, through an incision made in the patients, etc., and position 404 the device's jaws 202a, 202b adjacent a targeted tissue, e.g., over the targeted tissue. The end effector 204 can be inserted into the patient in the closed position, which can facilitate advancement of the end effector 204 into the patient through a relatively small opening. When positioned in the patient's body, the end effector 204 can be opened so as to allow the jaws 202a, 202b to be positioned on either side of the targeted tissue. The user can actuate 406 the closure trigger 208 by pulling the closure trigger 208 toward the stationary handle 224. The actuation 406 of the closure trigger 208 can cause the jaws 202a, 202b to close and clamp the targeted tissue therebetween.

As mentioned above, the device 200 can be configured to lock the closure trigger 208 in a fixed position relative to the stationary handle 224 and/or sense when the closure trigger 208 is in close proximity of the stationary handle 224. If the closure trigger 208 is unlocked and/or the sensor 220 senses that the closure trigger is open 408, the device 200 can disable 410 the motor 206 such that the motor 206 cannot be turned on to advance the cutting element and/or the compression member (e.g., an I-blade), if the motor 206 is not already so disabled. Also, a feathering algorithm 412 can be loaded, which can facilitate application of energy when the energy actuator 214 is actuated 424, as discussed further below. If the closure trigger 208 is locked and/or the sensor 220 senses that the closure trigger is closed 408, the device 200 can enable 414 the motor 206 such that the motor 206 can be turned on to advance the cutting element and/or the compression member (e.g., an I-blade), if the motor 206 is not already so enabled. The closure trigger being locked and/or closed can cause the controller to set 409 a latch flag indicating that the closure trigger 208 is closed and/or locked, and can cause the controller to load 411 a seal-only algorithm, e.g., retrieve the algorithm from a memory on board the device 200 or from an off-board memory in electronic communication with the device 200. The algorithm can allow the controller to apply 428 energy to the tissue, as discussed further below.

After the actuation 406 of the closure trigger 208 to close the jaws 202a, 202b, a sealing mode of the device 200 can be determined 416 to facilitate treatment of the clamped tissue. Sealing modes include grasping tissue, feathering tissue, touching up tissue, only sealing tissue, separately sealing and cutting tissue, and simultaneously sealing and cutting tissue. If the clamped tissue is not to be sealed, e.g., the mode includes grasping tissue, feathering tissue, or touching up tissue, then the user can perform any further desired tissue manipulation. The user can then release 418 the closure trigger 208 so as to open the jaws 202a, 202b. The jaws 202a, 202b can then be removed 420 from the targeted tissue. If the controller is configured to set a latch flag when the closure trigger 208 is closed, e.g., because the sensor 200 is configured to sense latch closure, then the latch flag can be cleared 421.

If the clamped tissue is to be sealed, the tissue can be separately cut and sealed or simultaneously cut and sealed. As mentioned above, the user can make this decision 422 based on any one or more factors, such as personal preference, type of surgical procedure being performed, type of the targeted tissue, etc. The user can indicate that the clamped tissue is to be separately sealed and cut by actuating 424 the energy actuator 214. When properly actuated 426, e.g., fully pressed down, the device 200 can apply 428 energy to the clamped tissue. The controller can cause 430 a first energy alert to be provided to the user indicating that energy is being applied to the tissue, since the user may not be able to visually, audibly, and/or tactilely verify that the energy is being applied. The first energy alert can be provided in a variety of ways, such as by emitting a sound, illuminating a light, etc.

The sensor 220 can be configured to measure 432 impedance of the tissue while the energy is being applied to the tissue. The impedance can be continuously monitored 432 during the application of the energy. Continuous monitoring of the impedance may not be precisely continuous, as will be appreciated by a person skilled in the art, due to, e.g., limitations in speed of digital processing. In other embodiments, the impedance can be measured at predetermined time intervals without being continuous monitoring. Measuring the impedance of the tissue during energy application thereto, either continuously or periodically, can allow the impedance to help determine a length of time to apply the energy to the tissue. If energy is being applied 438 to the tissue, and the closure trigger 208 is properly closed 440, and an absolute value of the impedance is determined 442 by the controller, e.g., as indicted by a signal from the sensor 200, to reach a predetermined threshold value, then the controller can cause 444 a second energy alert to be provided to the user indicating that energy application to the tissue is ceasing 446, since the user may not be able to visually, audibly, and/or tactilely verify that the energy is being applied. The second energy alert can be provided in a variety of ways, such as by emitting a sound, illuminating a light, etc. The second energy alert can be different than the first energy alert, e.g., be a different audible tone, be a differently colored illuminated light, etc., which can help the user know the condition being indicated by the alert. The impedance reaching the predetermined threshold value can, as discussed above, indicate that the tissue has been heated and "cooked" so as to be ready for cutting. After the energy stops 446, the device 200 can reset 448 so as to be ready for an optional subsequent actuation of the energy actuator 214.

Before the energy deactivates 446 automatically in response to the impedance limit being met, the user can stop 434 actuating the energy actuator 214, e.g., stop pressing the button, such that the energy actuator 214 ceases 436 being actuated. This allows more user control of tissue sealing, as experienced users can have a sense of and/or personal preference for how long energy should be applied to tissue.

If the user stops 434 actuating the energy actuator or if the tissue is not being separately sealed and cut, the tissue may be subject 450 to being simultaneously sealed and cut. If the clamped tissue is not to be simultaneously sealed and cut, then the user can perform any further desired tissue manipulation. The user can then release 418 the closure trigger 208 so as to open the jaws 202a, 202b, and the jaws 202a, 202b can be removed 420 from the targeted tissue.

If the clamped tissue is to be simultaneously sealed and cut, the user can actuate 452 the closure trigger 408 to close the end effector 404, if not already closed, and lock the closure trigger 408 in place if the device 200 is configured to so lock the closure trigger 408. The user can then actuate 454 the firing trigger 210 so as to cause the cutting element to translate along the end effector 204 and cut the clamped tissue. The actuation 454 of the firing trigger can also cause energy to be applied to the clamped tissue such that the tissue is being simultaneously sealed and cut. While the firing actuator 210 is being actuated 454, the device 200 can be configured to control speed of the cutting element's translation along the end effector 204 so as to control a speed of the tissue's cutting. As discussed above, the device 200 can be configured to control the cutting element's speed based at least in part on an amount of user input to the firing actuator 210.

With reference to the continuum embodiment of FIG. 11, if the amount of input is determined 456 to be in the "Reverse" zone, then the controller can cause the motor 206 to provide power that retracts 458 the cutting element to its initial home position, e.g., moves the cutting element proximally along the end effector 204 to the start position. In this way, whenever the cutting element can be returned to its start position whenever the end effector is opened, e.g., when the closure trigger 208 is opened. This can help prevent the cutting element from being exposed and accidentally cutting tissue and/or other matter near the end effector, which is not closed when the closure trigger is not closed. The sensor 220 can be configured to monitor 460 a position of the cutting element relative to the end effector 204. The controller can be configured to receive an output from the sensor 220 indicating the position, which the controller can use in controlling the motor's output to reverse 462 the cutting element. If the amount of input is determined 464 to be in the "Hold" zone, then the controller can cause the motor 206 to not 466 provide power to the cutting element such that the cutting element does not move relative to the end effector 204. Being determined 464 to be in the "Hold" zone can cause the controller to load 492 a simultaneous seal and cut algorithm, e.g., retrieve the algorithm from a memory on board the device 200 or from an off-board memory in electronic communication with the device 200. The algorithm can allow the controller to apply 494 energy to the tissue before the cutting element begins to cut the tissue, e.g., before the amount of input enters the "Forward" zone. This heating or "cooking" of the tissue before the tissue begins to be cut can make the tissue easier to cut, which can allow the motor to provide less power than it would need to provide if the tissue were not pre-heated by the energy application, and/or can help subject a compression member attached to the cutting element to lower forces, which can help prevent damage thereto. The motor can thus perform more efficiently and/or can be a smaller motor than needed without the pre-heating. Similar to that discussed above, the controller can cause 496 the first energy alert to be provided to the user indicating that energy is being applied to the tissue, and impedance can be measured 498 while the energy is being applied to the tissue. If the user input is determined 500 to move from the "Hold" zone to the "Reverse" zone, then energy application can cease 482, as discussed further below. If the user input is not determined 500 to move from the "Hold" zone to the "Reverse" zone, then the user input is presumed to be in the "Hold" zone or the "Forward" zone, so energy application can continue until it is determined 502 that the cutting element has been fully deployed, e.g., reached its end position. Energy can thus be applied in the "Hold" and "Forward" zones but not in the "Reverse zone." The controller can then determine 478 whether or not the tissue has reached its predetermined threshold value of impedance, e.g., a target impedance, as discussed further below.

If the amount of input is determined 464 to not be in the "Hold" zone but is determined 468 to be in the "Forward" zone, then the controller can cause the motor 206 to provide power that advances 470 the cutting element from its initial home position, e.g., moves the cutting element distally along the end effector 204. The sensor 220 can be configured to monitor 472 the position of the cutting element relative to the end effector 204. The controller can be configured to receive an output from the sensor 220 indicating the position, which the controller can use in controlling the motor's output to advance 474 the cutting element and in controlling the motor's output to stop 476 the forward advancement of the cutting element when the cutting element reaches its end position.

When the forward advancement 474 of the cutting element stops 476, the controller can determine 478 whether or not the tissue has reached its predetermined threshold value of impedance, e.g., a target impedance. If the tissue has not reached the predetermined threshold value of impedance, that can indicate that the tissue has not been adequately sealed. The device 200 can thus apply 428 energy to the clamped tissue. If energy is already being applied to the tissue, energy can continue being applied. If energy is not already being applied, then energy application can begin. If the tissue has reached the predetermined threshold value of impedance, then the controller can cause 480 a third energy alert to be provided to the user indicating that cutting of and energy application to the tissue is ceasing 446, since the user may not be able to visually, audibly, and/or tactilely verify that the energy is being applied or that cutting is occurring. The controller can stop 482 energy application since the tissue has been determined to have been cut and sealed. The device 200 can reset 484 so as to be ready for a next cycle of energy application, such as when a second tissue is clamped between the jaws.

After actuating 454 the firing trigger 210 so as to cause the cutting element to translate along the end effector 204 and cut the clamped tissue, as discussed above, the user can release 486 the firing trigger 210. The release 486 of the firing trigger 210 can cause, with reference to the continuum embodiment of FIG. 11, the user input to the firing trigger 210 to move from the "Forward" zone to the "Hold" zone, and from the "Hold" zone to the "Reverse" zone. Entering 488 the "Reverse" zone can cause 490 the cutting element to be retracted, e.g., by the controller causing the motor to reverse direction so as to reverse movement of the cutting element from a distal cutting direction to a proximal retraction direction. The cutting element being refracted to its start position can trigger the device 200 to reset 484 so as to be ready for a next cycle of energy application.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
an end effector including first and second jaws configured to engage tissue between facing engagement surfaces thereof;
a sensor configured to sense an impedance of the tissue engaged between the facing engagement surfaces;
a cutting element configured to cut the tissue engaged between the facing engagement surfaces;
a motor configured to provide an output that causes the cutting element to translate through the end effector at a speed; and
a controller configured to change an output of the motor based at least in part on the sensed tissue impedance, thereby controlling the speed of the cutting element translating through the end effector,
wherein when the cutting element is cutting the tissue, the controller is configured to control the output of the motor such that the output of the motor cannot exceed 80% of a total output capability of the motor; and after the cutting element has cut the tissue, the controller is configured to control the output of the motor such that the output of the motor is allowed to exceed 80% of the total output capability of the motor.

2. The device of claim 1, wherein the controller is configured to change the output of the motor in real time with the cutting element translating through the end effector.

3. The device of claim 1, wherein the controller is configured to prevent a velocity of the motor from exceeding a predetermined maximum threshold velocity during the translation of the cutting element through the end effector based at least in part on at least one of a current of the motor, a voltage of the motor and on revolutions per minute (RPM) of the motor, the current, the voltage, and the RPM being proportional to a load of the cutting element.

4. The device of claim 1, wherein the controller is configured to repeatedly and sequentially increase and decrease a velocity of the motor in response to the velocity of the motor reaching a predetermined threshold velocity, the repeated sequential increasing and the decreasing of the velocity continuing until the velocity of the motor falls below the predetermined threshold velocity.

5. The device of claim 1, wherein the controller is configured to cause a feedback signal to be provided to a user, the feedback signal being indicative of the speed of the cutting element, and the feedback signal including at least one of a light, a sound, a vibration, and a visual textual display.

6. The device of claim 1, wherein the sensor is configured to sense a reference tissue impedance of the tissue engaged between the facing engagement surfaces, and
when the cutting element is translating through the end effector and the sensed tissue impedance becomes greater than the reference tissue impedance, the controller is configured to change the output of the motor so as to speed up the translation of the cutting element through the end effector, and
when the cutting element is translating through the end effector and the sensed tissue impedance becomes less than the reference tissue impedance, the controller is configured to change the output of the motor so as to slow down the translation of the cutting element through the end effector.

7. The device of claim 1, wherein the sensor is disposed within a housing of the surgical device that is configured to be handheld by a user.

8. The device of claim 1, wherein the sensor is remotely located from a housing of the surgical device that is configured to be handheld by a user, the sensor being configured to be in electronic communication with the controller from the remote location.

9. The device of claim 1, further comprising a handle configured to be actuated by a user so as to move the first and second jaws from an open position to a closed position, the controller being configured to prevent the translation of the cutting element through the end effector until the first and second jaws are in the closed position.

10. The device of claim 1, wherein the controller is also configured to change the output of the motor based at least in part on a linear force of the cutting element moving through the tissue.

11. The device of claim 10, wherein the controller is configured to calculate the linear force in real time with the cutting element moving through the tissue based on one or more of the current of the motor, the voltage of the motor, the RPM of the motor, and the drivetrain of the motor.

12. The device of claim 1, further comprising a second sensor configured to sense a longitudinal position of the cutting element relative to the end effector; and
wherein the controller is configured to change the output of the motor based at least in part on the sensed longitudinal position of the cutting element relative to the end effector.

13. The device of claim 12, wherein the cutting element is configured to translate through the end effector from a start position to an end position, and the controller is configured to change the output of the motor in response to the second sensor sensing that the cutting element translates through an intermediate position that is between the start and end positions along a longitudinal axis of the end effector.

14. The device of claim 1, further comprising a second sensor configured to sense a longitudinal position of the cutting element relative to the end effector; and
wherein the controller is configured to close the first and second jaws at a rate proportional to the sensed longitudinal position.

15. The device of claim 1, further comprising a housing having the sensor, the controller, and the motor disposed therein.

16. The device of claim 1, further comprising a housing having the sensor and the controller disposed therein; and
wherein the motor is located outside the housing and is in electronic communication with the cutting element.

17. A surgical device, comprising:
a proximal handle portion operatively coupled to a motor;
a shaft extending distally from the handle portion;
an end effector at a distal end of the shaft, the end effector being configured to engage tissue;
a cutting element configured to move longitudinally through the end effector from a start position to an end position, the motor being configured to provide power that causes the movement of the cutting element from the start position to the end position;

a sensor configured to sense a position of the cutting element relative to the end effector; and a controller configured to adjust the power provided by the motor during the movement of the cutting element based at least in part on the sensed position of the cutting element relative to the end effector, wherein when the cutting element is cutting the tissue, the controller is configured to control the output of the motor such that the output of the motor cannot exceed 80% of a total output capability of the motor; and after the cutting element has cut the tissue, the controller is configured to control the output of the motor such that the output of the motor is allowed to exceed 80% of the total output capability of the motor.

18. The device of claim 17, wherein the controller is configured to prevent the power from causing a force of the cutting element moving longitudinally through the tissue to exceed a maximum threshold amount of force in response to the sensor sensing the position of the cutting element as being at or beyond a predetermined intermediate position that is between the start and end positions.

19. The device of claim 18, wherein the force is based on one or more of a current of the motor, a voltage of the motor, revolutions per minute (RPM) of the motor, and drivetrain of the motor.

20. The device of claim 17, wherein the controller is configured to close the end effector at a rate proportional to the sensed position.

21. The device of claim 17, further comprising a second sensor configured to sense an impedance of the tissue engaged by the end effector; and wherein the controller is configured to adjust the power provided by the motor during the movement of the cutting element based at least in part on the sensed tissue impedance, thereby adjusting a velocity of the cutting element moving longitudinally through the end effector.

22. A surgical method, comprising:

engaging tissue with first and second jaws of a surgical device;

receiving an input from a user that causes a motor of the device to provide power that causes a cutting element to move along the first and second jaws so as to cut the engaged tissue;

measuring an impedance of the engaged tissue in real time with the cutting element moving along the first and second jaws; and changing an amount of the power provided by the motor based at least in part on the measured tissue impedance, wherein the surgical device comprises a controller configured to change an output of the motor based at least in part on the sensed tissue impedance, thereby controlling the speed of the cutting element translating through the end effector, wherein when the cutting element is cutting the tissue, the controller is configured to control the output of the motor such that the output of the motor cannot exceed 80% of a total output capability of the motor; and after the cutting element has cut the tissue, the controller is configured to control the output of the motor such that the output of the motor is allowed to exceed 80% of the total output capability of the motor.

23. The method of claim 22, further comprising sensing a longitudinal position of the cutting element relative to the first and second jaws; and performing at least one of:

changing the amount of the power provided by the motor based at least in part on the sensed longitudinal position of the cutting element relative to the first and second jaws, and closing the first and second jaws at a rate proportional to the sensed position.

\* \* \* \* \*